United States Patent
Lee et al.

(10) Patent No.: US 7,351,481 B2
(45) Date of Patent: Apr. 1, 2008

(54) IMIDAZOLE RING-CONTAINING COMPOUND AND ORGANIC ELECTROLUMINESCENCE DISPLAY DEVICE

(75) Inventors: Seok-Jong Lee, Suwon-si (KR);
Young-Kook Kim, Suwon-si (KR);
Seok-Hwan Hwang, Suwon-si (KR);
Seung-Gak Yang, Suwon-si (KR);
Hee-Yeon Kim, Suwon-si (KR);
Young-Rag Do, Seoul (KR); Joo-Han Song, Suwon-si (KR)

(73) Assignee: Samsung SDI Co., Ltd., Suwon (KR)

( * ) Notice: Subject to any disclaimer, the term of this patent is extended or adjusted under 35 U.S.C. 154(b) by 421 days.

(21) Appl. No.: 10/958,542

(22) Filed: Oct. 6, 2004

(65) Prior Publication Data
US 2005/0074632 A1    Apr. 7, 2005

(30) Foreign Application Priority Data
Oct. 7, 2003    (KR) .................. 10-2003-0069702

(51) Int. Cl.
*H01L 51/54*    (2006.01)
*C09K 11/06*    (2006.01)
*C07D 513/00*    (2006.01)

(52) U.S. Cl. .................. 428/690; 428/917; 313/504; 313/506; 257/40; 257/E51.024; 257/E51.026; 257/E51.05; 548/154; 548/161; 548/303.1; 548/440

(58) Field of Classification Search .............. 548/154, 548/440, 445
See application file for complete search history.

(56) References Cited

U.S. PATENT DOCUMENTS

| | | | | |
|---|---|---|---|---|
| 3,455,924 A | * | 7/1969 | Lednicer | 544/281 |
| 5,552,422 A | * | 9/1996 | Gauthier et al. | 514/368 |
| 6,551,723 B1 | | 4/2003 | Okada et al. | |
| 2002/0183320 A1 | * | 12/2002 | Gerlach et al. | 514/234.5 |

FOREIGN PATENT DOCUMENTS

JP    11-106340    4/1999

* cited by examiner

*Primary Examiner*—Dawn Garrett
*Assistant Examiner*—Brett A Crouse
(74) *Attorney, Agent, or Firm*—H.C. Park & Associates, PLC

(57) ABSTRACT

The present invention is related to an imidazole ring-containing compound and an organic electroluminescence (EL) display device using the same. In particular, the imidazole ring-containing compound may be used alone or in combination with a dopant as a material for organic films such as an electroluminescent layer. The organic EL display device using an organic film made of the imidazole ring-containing compound has improved characteristics such as luminance, efficiency, driving voltage, and color purity.

7 Claims, 6 Drawing Sheets

US 7,351,481 B2

IMIDAZOLE RING-CONTAINING COMPOUND AND ORGANIC ELECTROLUMINESCENCE DISPLAY DEVICE

CROSS-REFERENCE TO RELATED APPLICATIONS

This application claims priority to Korean Patent Application No. 2003-69702, filed on Oct. 7, 2003, in the Korean Intellectual Property Office, the disclosure of which is incorporated herein in its entirety by reference.

FIELD OF THE INVENTION

The present invention is related to an imidazole ring-containing compound and an organic electroluminescence display device using the same. In particular, the present invention is related to a high-efficiency, high-luminance, and low-power consumption organic electroluminescence display device that is manufactured using an imidazole ring-containing compound as a host of a phosphorescent or fluorescent dopant in various colors such as red, green, blue, etc.

BACKGROUND

Electroluminescent (EL) devices, known as self-luminous displays, provide a wider viewing angle, higher contrast, and shorter response time. EL devices can be classified depending on the material used for the electroluminescent layer as inorganic or organic EL devices. As compared with inorganic EL devices, organic EL devices provide higher luminance, lower driving voltage, shorter response time, and the ability to display a wider range of colors.

A typical organic EL device includes an anode on the top surface of a substrate. A hole transporting layer, an electroluminescent layer, an electron transporting layer, and a cathode are formed sequentially on the anode. The hole transporting layer, the electroluminescent layer, and the electron transporting layer are thin films made of organic compounds.

Organic EL devices with the above-described structure operate according to the following principles. When a voltage is applied across the anode and the cathode, holes injected from the anode migrate via the hole transporting layer into the electroluminescent layer. Electrons injected from the cathode migrate via the electron transporting layer into the electroluminescent layer and combine with the holes therein to generate excitons. When the excitons transit from an excited state to a base state, molecules in the electroluminescent layer emit light to form visible images. Light emission occurring as excitons transiting from a singlet state (S1) to a base (S0) state is referred to as "fluorescence", and light emission occurring as excitons transiting from a triplet (T1) state to a base state is referred to as "phosphorescence". In fluorescence, only 25% of the singlet state excitons (75% of triplet state excitons) are used, thereby limiting emission efficiency. In contrast, in phosphorescence 75% of triplet state excitons and 25% of singlet state excitons are used so that 100% internal quantum efficiency can be theoretically achieved.

A high-efficiency, green and red organic EL device has been developed using Ir(ppy)$_3$, which is a phosphorescent colorant having a heavy atom such as Ir or Pt with strong spin-orbit bond and PtOEP as dopants to enable effective light emission in a triplet (phosphorescent) state. In the organic EL device CBP (4,4'-N,N'-dicarbazole-biphenyl) is used as a host. This organic EL device, however, has a short lifespan of 150 hours because the CBP has a low glass transition temperature of 110° C. and is liable to be crystallized, making it unsuitable for commercial use.

SUMMARY OF THE INVENTION

The present invention is directed to a host material suitable for fluorescent and phosphorescent dopants of any color such as red, green, blue, and white, which has improved electrical stability, better charge transporting capability, a high glass transition temperature, and does not crystallize. Moreover, the present invention is also related to a high-efficiency, low-voltage, high-luminance, long-lifespan organic EL device.

According to an aspect of the present invention, an imidazole ring-containing compound of Formula (1) below is provided:

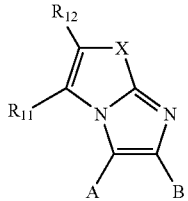

Formula 1 where A may be, for example, any compound illustrated below:

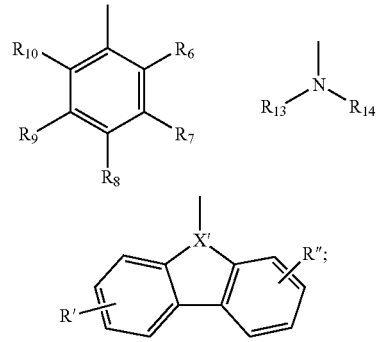

where B may include, but is not limited to, a compound depicted below:

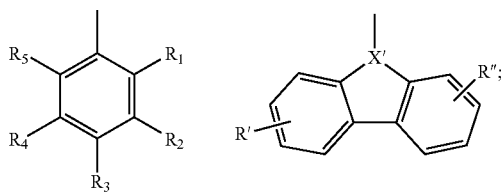

where X may be O, NH, S, or Se; X' may be CR or N; where each of $R_1$ through $R_{12}$ may independently be, for example, a hydrogen, a substituted or unsubstituted C1-C30 alkyl group, a substituted or unsubstituted C1-C30 alkoxy group, a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, or a substituted or unsubstituted C1-C30 alkylsulfonyl group, for and where the adjacent groups among $R_1$ through $R_{12}$ may combine together to form a substituted or unsubstituted C2-C30 saturated or unsaturated ring.

Moreover, each of R' and R", which may be a monosubstituted or multi-substituted group, may be a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, where R' and R" may combine together to form a saturated or unsaturated ring; and where each of $R_{13}$ and $R_{14}$ may independently be, for example, a substituted or unsubstituted C1-C30 alkyl group, a substituted or unsubstituted C6-C30 aryl group, or a substituted or unsubstituted C3-C30 heteroaryl group.

According to another aspect of the present invention, there is provided an organic EL device that may include an organic film containing the above-described imidazole ring-containing compound between a pair of electrodes.

BRIEF DESCRIPTION OF THE DRAWINGS

The above and other features and advantages of the present invention will become more apparent by describing in detail exemplary embodiments thereof with reference to the attached drawings.

DETAILED DESCRIPTION OF THE INVENTION

Figure 1:
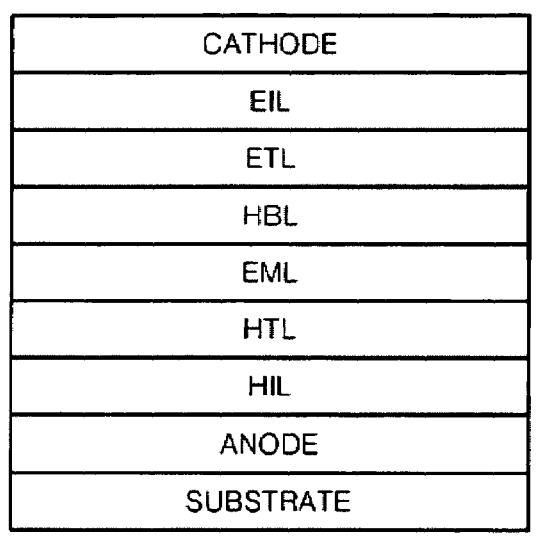
FIG. 1 is a sectional view of a general organic EL display device.

According to an embodiment of the present invention, adjacent groups among $R_1$ through $R_{12}$ in Formula (1) as described above, may combine together to form a substituted or unsubstituted C2-C30 saturated or unsaturated ring. This saturated or unsaturated ring may be a substituted or unsubstituted C6-C30 aryl group, a substituted or unsubstituted C6-C30 condensed polycyclic group or a substituted or unsubstituted C2-C30 heteroaryl group, for example. Examples of these groups include, but are not limited to, a phenyl group and a naphthalene group.

In a further embodiment, the compound of Formula (1) may be one of the compounds of Formula (2) through (13), as illustrated below, depending on the combination of A and B.

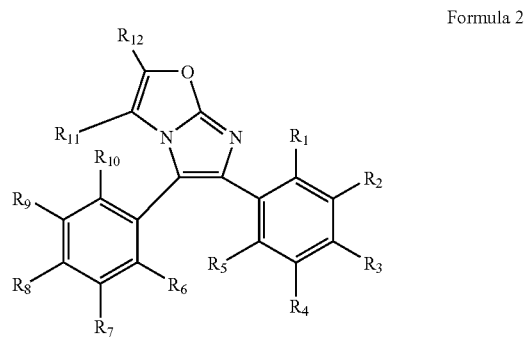

Formula 2

In Formula (2) above, $R_1$ through $R_{10}$ may be the same as described above, and both $R_{11}$ and $R_{12}$ may be hydrogen or may combine together to form a substituted or unsubstituted C2-C30 saturated or unsaturated ring.

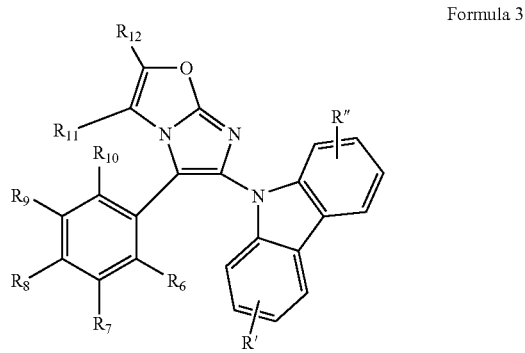

Formula 3

In Formula (3) above, $R_6$ through $R_{10}$ may be the same as described above, both $R_{11}$ and $R_{12}$ may be hydrogen or may

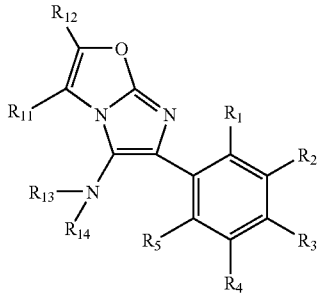

Formula 4

In Formula (4) above, $R_1$ through $R_5$ may be the same as described above, both $R_{11}$ and $R_{12}$ may be hydrogen or may combine together to form a substituted or unsubstituted C2-C30 saturated or unsaturated ring, and each of $R_{13}$ and $R_{14}$ may independently be a substituted or unsubstituted C6-C30 aryl group or a substituted or unsubstituted C2-C30 heteroaryl group.

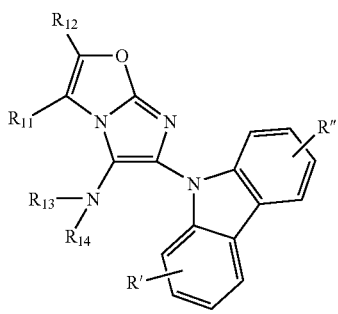

Formula 5

In Formula (5) above, both $R_{11}$ and $R_{12}$ may be hydrogen or may combine together to form a substituted or unsubstituted C2-C30 saturated or unsaturated ring, each of $R_{13}$ and $R_{14}$ may independently be a substituted or unsubstituted C6-C30 aryl group or a substituted or unsubstituted C2-C30 heteroaryl group, and both R' and R" may be hydrogen.

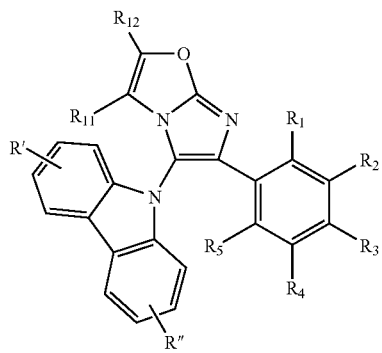

Formula 6

In Formula (6) above, $R_1$ through $R_5$ may be the same as described above, both $R_{11}$ and $R_{12}$ may be hydrogen or may combine together to form a substituted or unsubstituted C2-C30 saturated or unsaturated ring, and both R' and R" may be hydrogen.

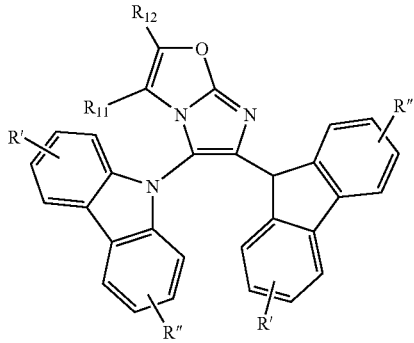

Formula 7

In Formula (7) above, both $R_{11}$ and $R_{12}$ may be hydrogen or may combine together to form a substituted or unsubstituted C2-C30 saturated or unsaturated ring, and R' and R" may be the same as described above.

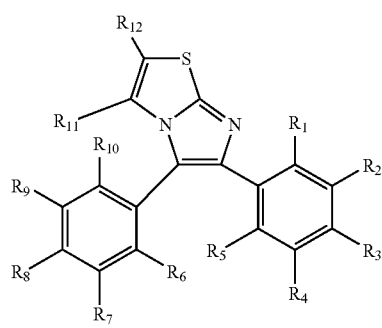

Formula 8

In Formula (8) above, $R_1$ through $R_{10}$ may be the same as described above, and both $R_{11}$ and $R_{12}$ may be hydrogen or may combine together to form a substituted or unsubstituted substituted C2-C30 saturated or unsaturated ring.

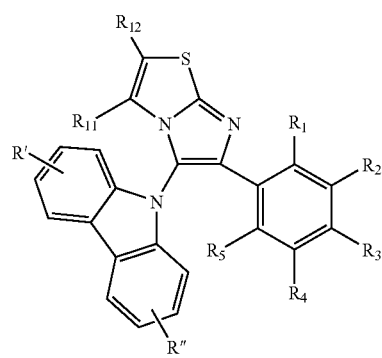

Formula 9

In Formula (9) above, $R_1$ through $R_5$ may be the same as described above, both $R_{11}$ and $R_{12}$ may be hydrogen or may combine together to form a substituted or unsubstituted C2-C30 saturated or unsaturated ring, and both R' and R" may be hydrogen.

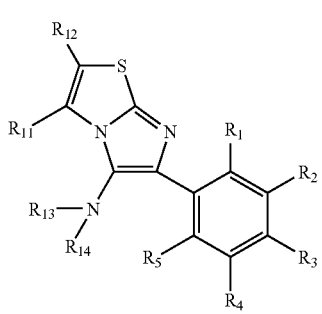

Formula 10

In Formula (10) above, $R_1$ through $R_5$ may be the same as described above, both $R_{11}$ and $R_{12}$ may be hydrogen or may combine together to form a substituted or unsubstituted C2-C30 saturated or unsaturated ring, and each of $R_{13}$ and $R_{14}$ may independently be a substituted or unsubstituted C6-C30 aryl group or a substituted or unsubstituted C2-C30 heteroaryl group.

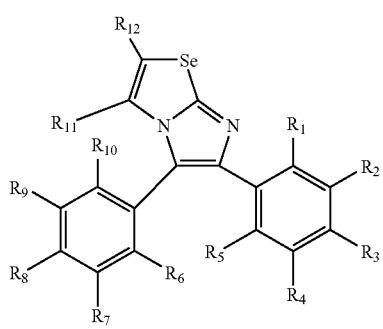

Formula 11

In Formula (11) above, $R_1$ through $R_{10}$ may be the same as described above, and both $R_{11}$ and $R_{12}$ may be hydrogen or may combine together to form a substituted or unsubstituted C6-C30 saturated or unsaturated ring.

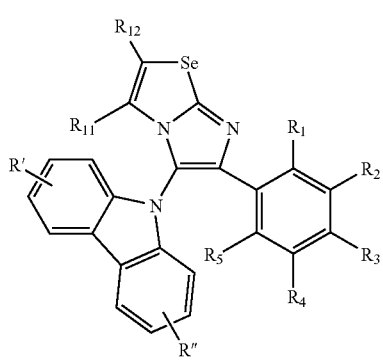

Formula 12

In Formula (12) above, $R_1$ through $R_5$ may be the same as described above, both $R_{11}$ and $R_{12}$ may be hydrogen or may combine together to form a substituted or unsubstituted C2-C30 saturated or unsaturated ring, and both R' and R" may be hydrogen.

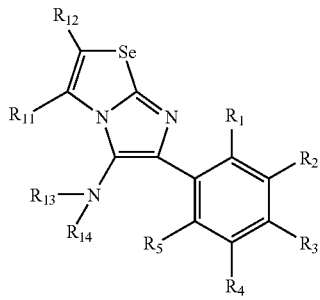

Formula 13

In Formula (13) above, $R_1$ through $R_5$ may be the same as described above, both $R_{11}$ and $R_{12}$ may be hydrogen or may combine together to form a substituted or unsubstituted C2-C30 saturated or unsaturated ring, and each of $R_{13}$ and $R_{14}$ may independently be a substituted or unsubstituted C6-C30 aryl group or a substituted or unsubstituted C2-C30 heteroaryl group.

In another embodiment, examples of the compound of Formula (2) above may include, but are not limited to, the compounds as illustrated below.

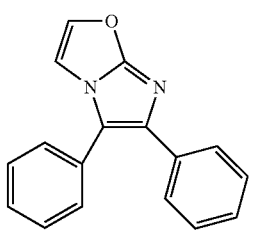

II-1

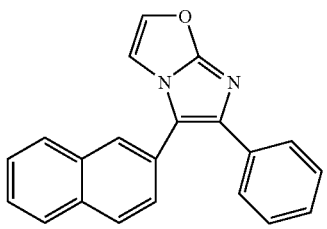

II-2

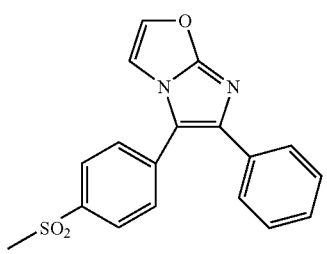

II-3

-continued
II-4
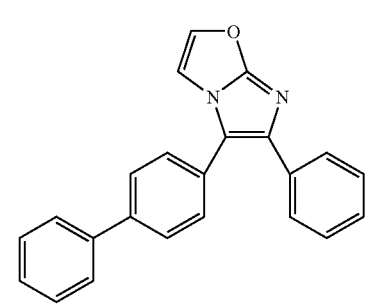
II-5
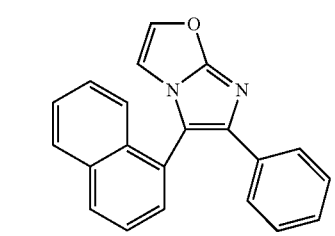
II-6
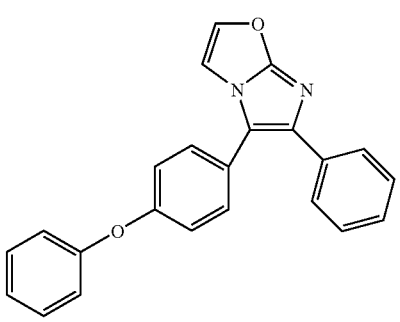
II-7
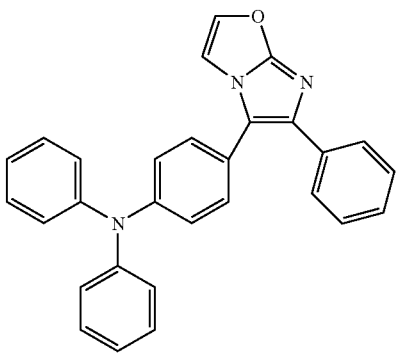
II-8
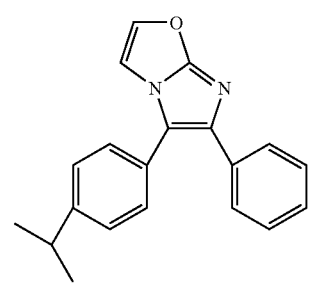
-continued
II-9
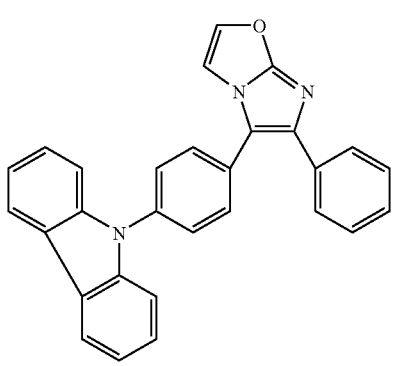
II-10
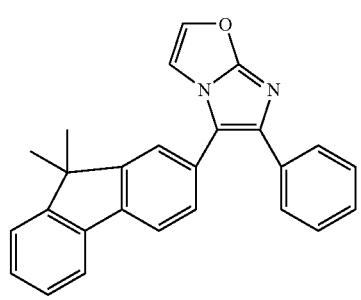
II-11
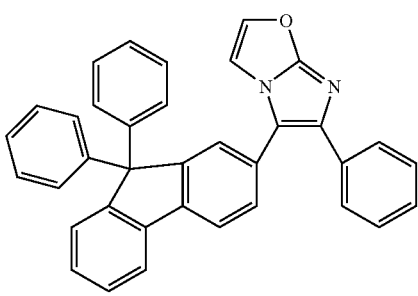
II-12
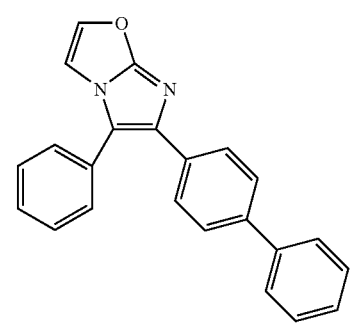
II-13
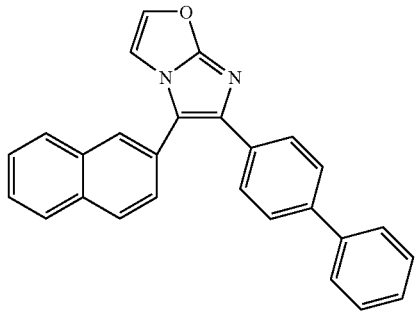

-continued
II-14
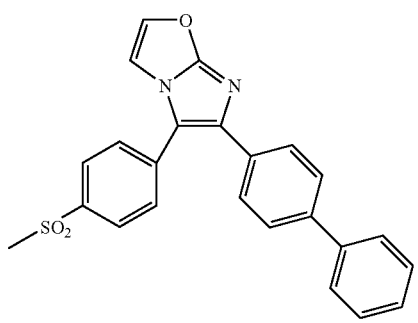
II-15
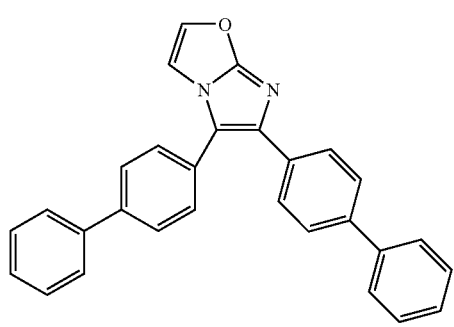
II-16
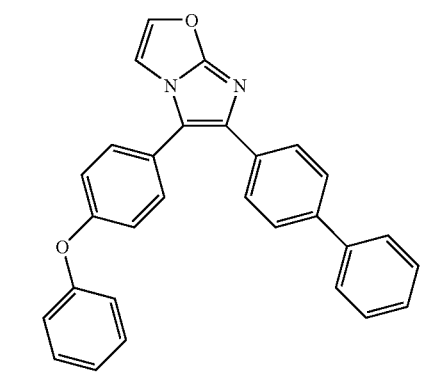
II-17
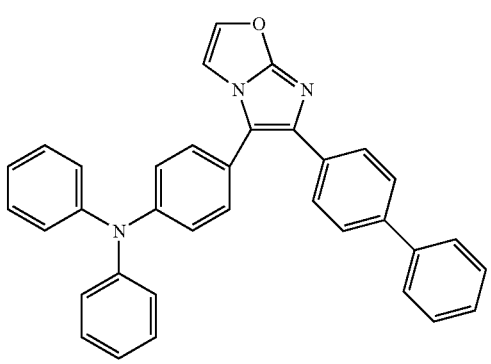
-continued
II-18
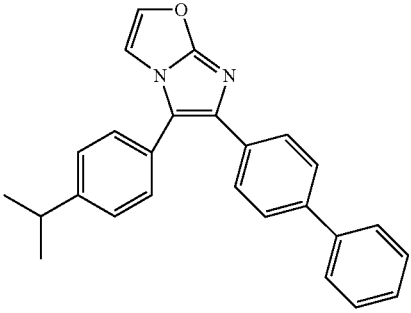
II-19
II-20
II-21
II-22

II-23 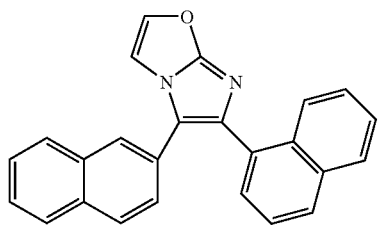
II-24 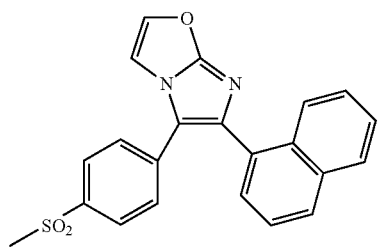
II-25 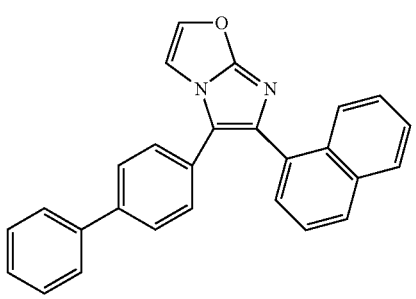
II-26 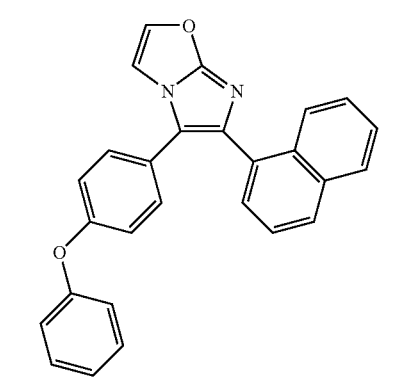
II-27 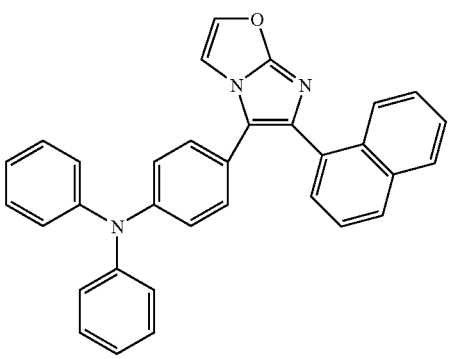
II-28 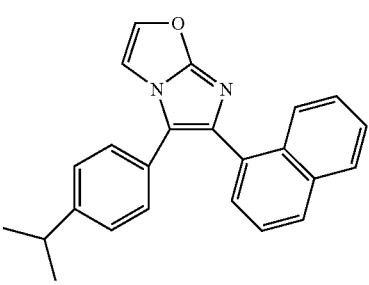
II-29 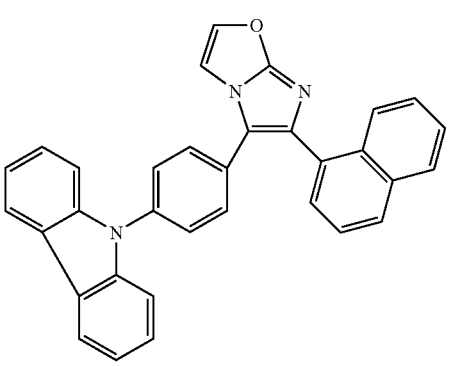
II-30 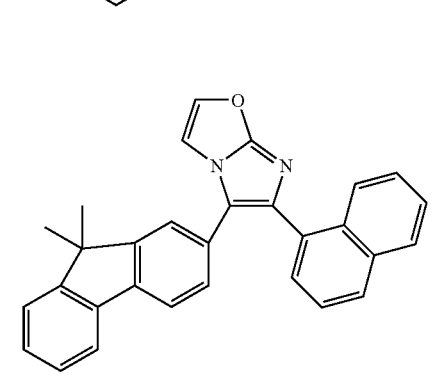
II-31 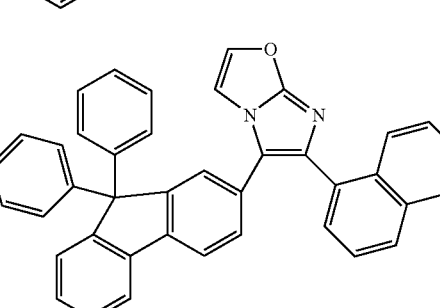
II-32 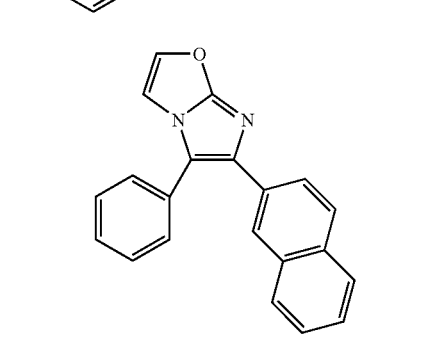

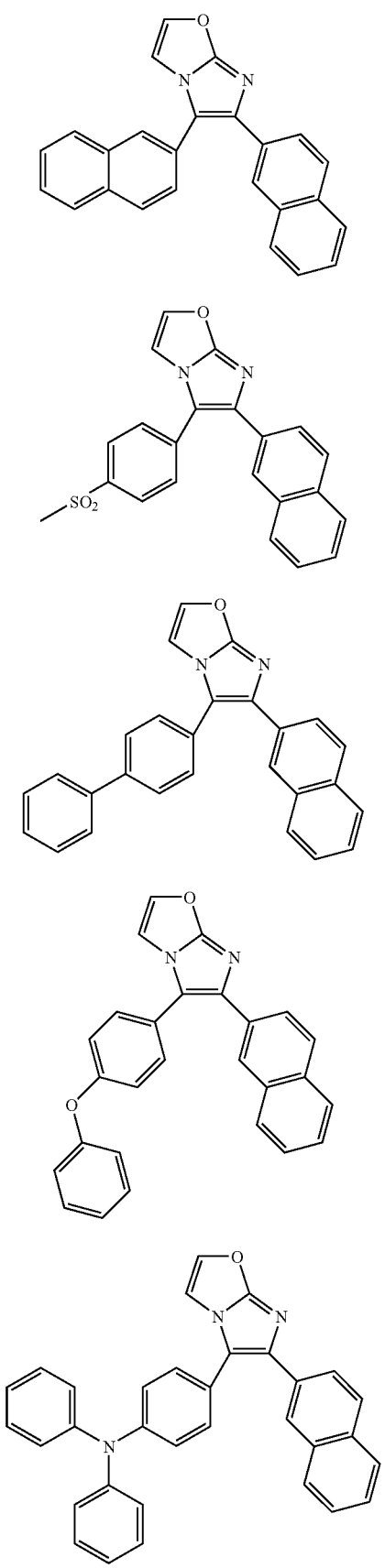
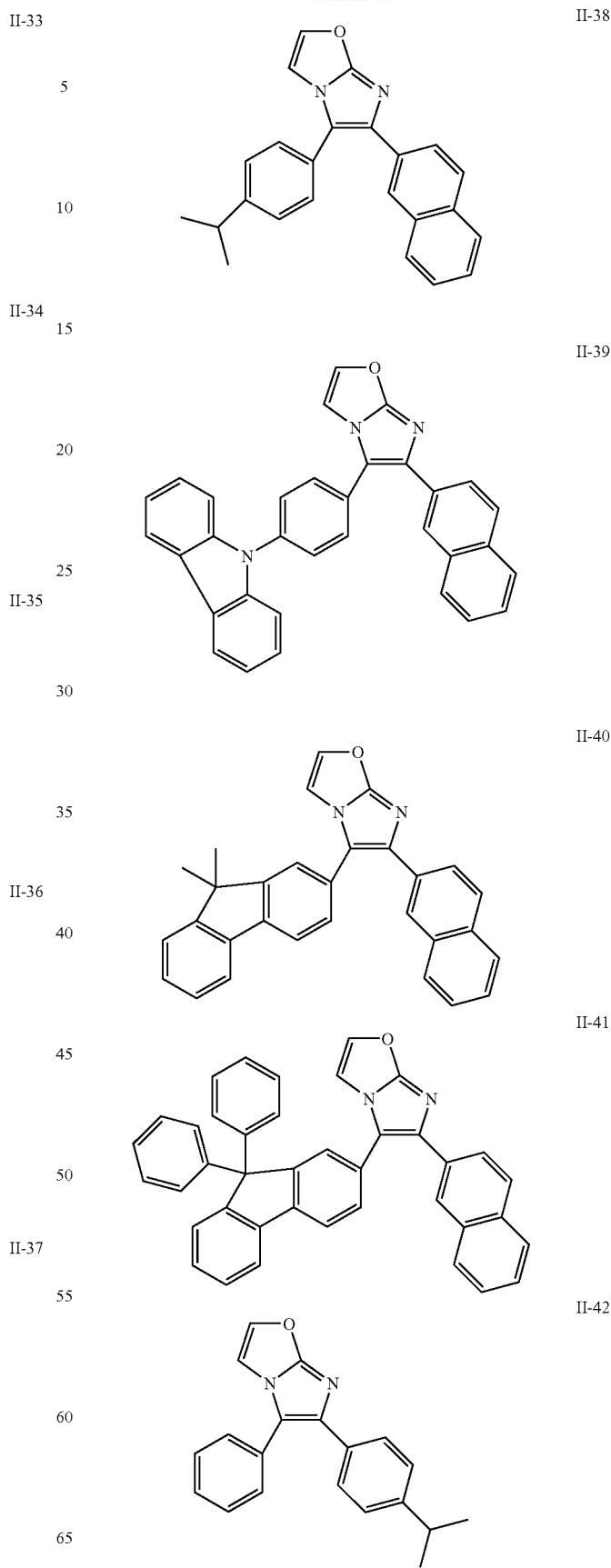

II-43
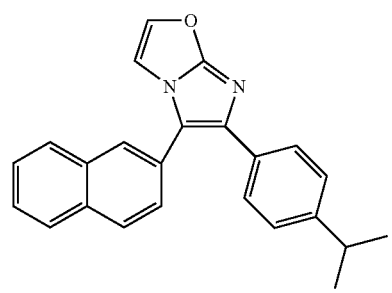
II-44
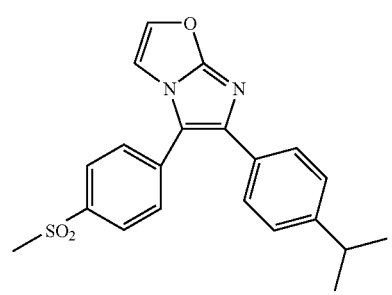
II-45
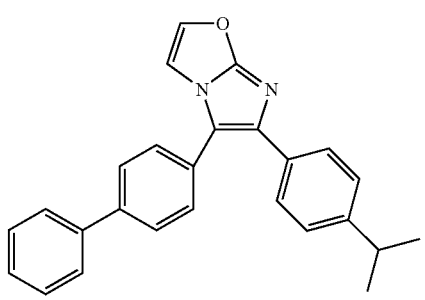
II-46
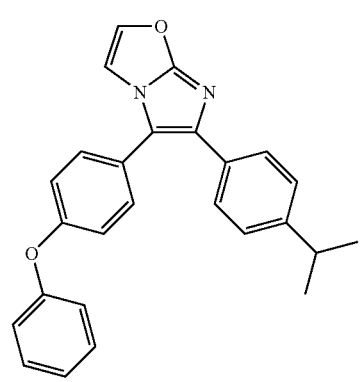
II-47
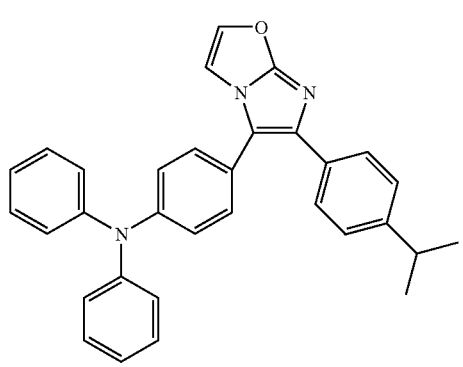
II-48
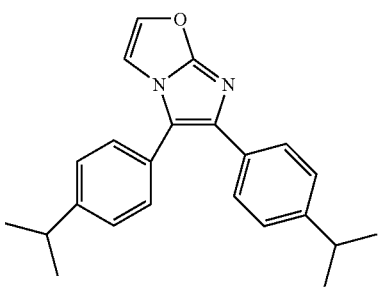
II-49
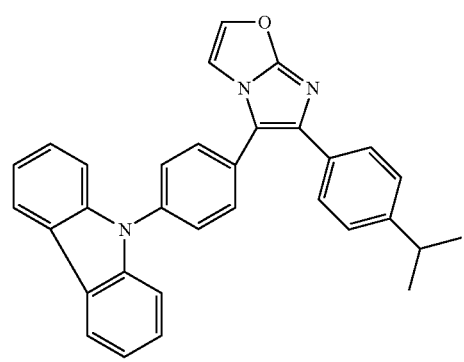
II-50
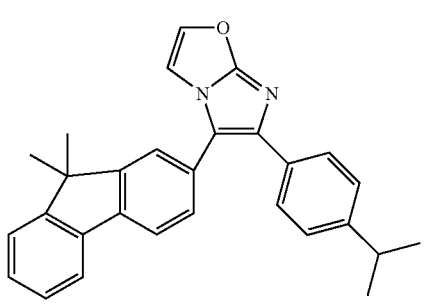
II-51
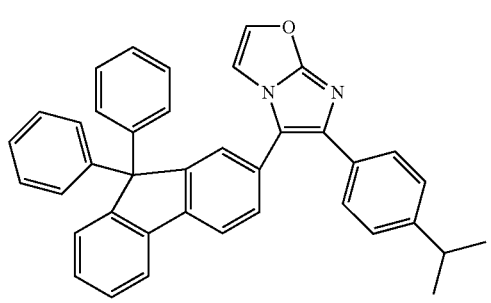
II-52
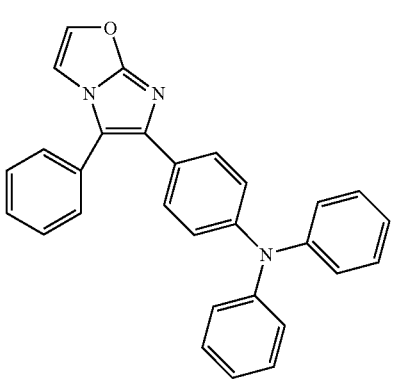

-continued
II-53
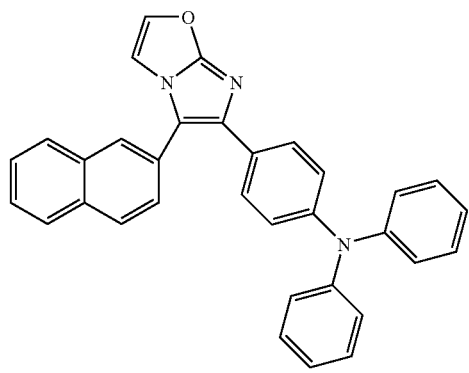
II-54
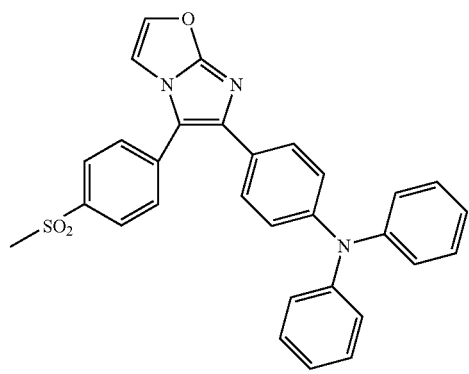
II-55
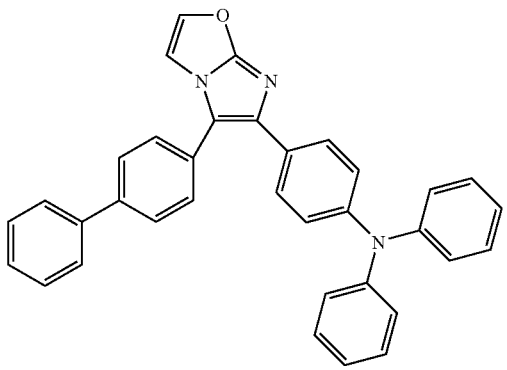
II-56
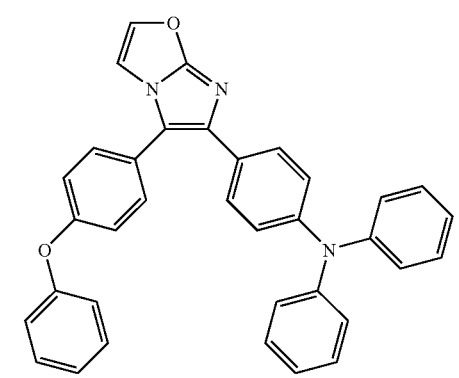
-continued
II-57
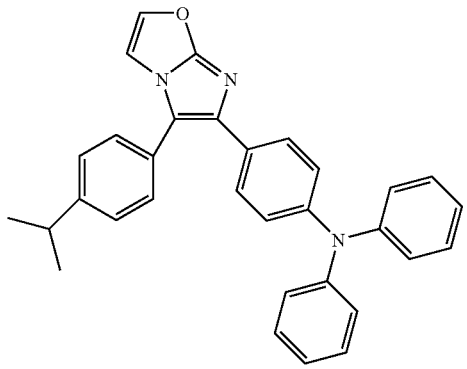
II-58
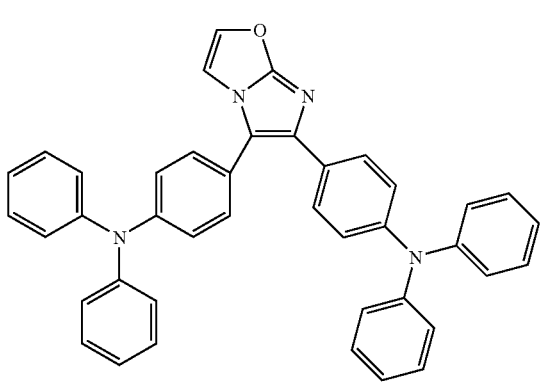
II-59
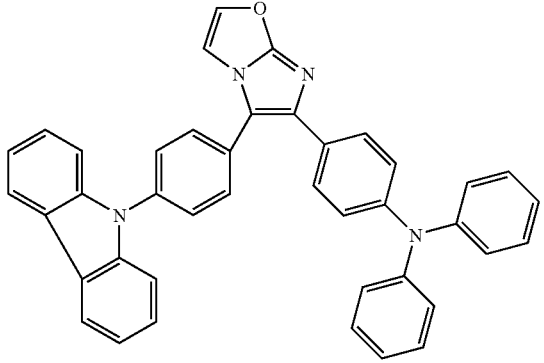
II-60
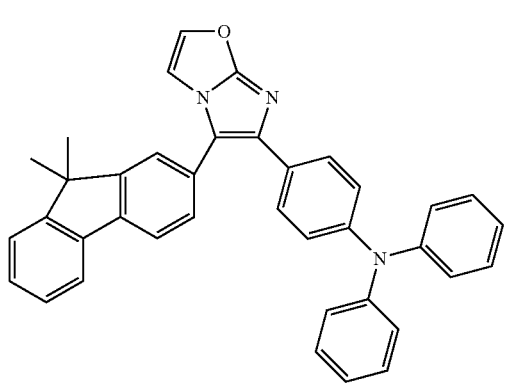

-continued
II-61
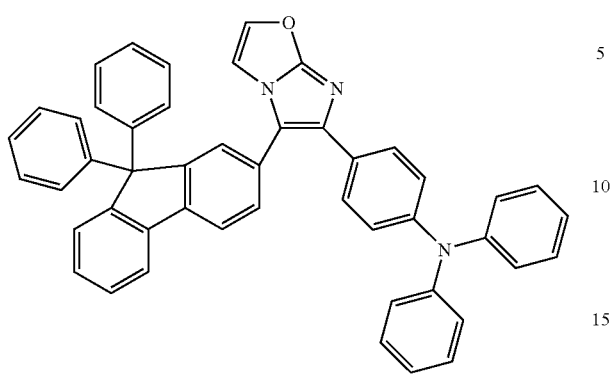
II-72
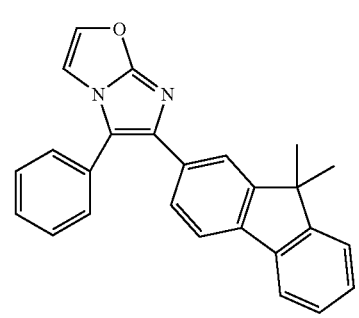
II-73
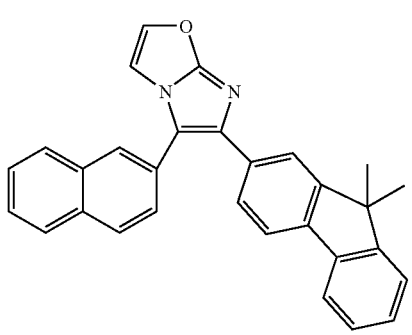
II-74
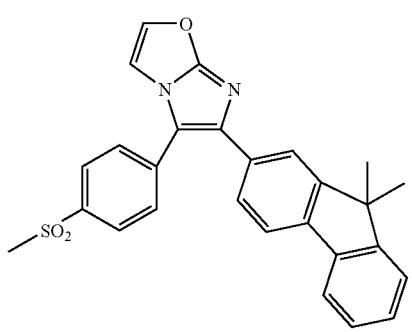
-continued
II-75
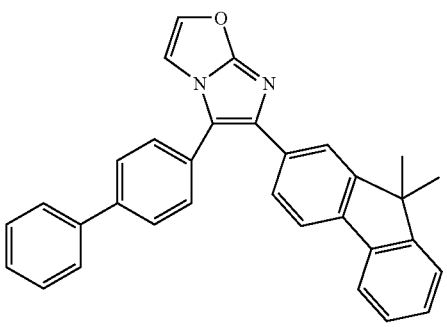
II-76
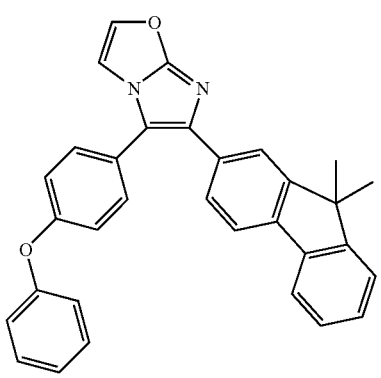
II-77
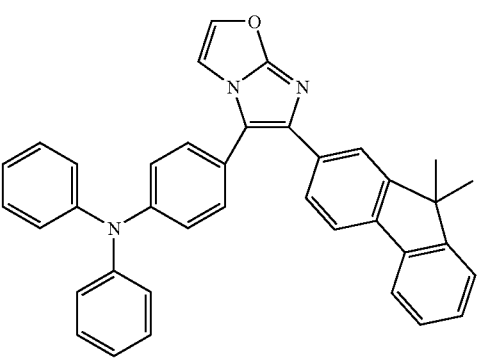
II-78
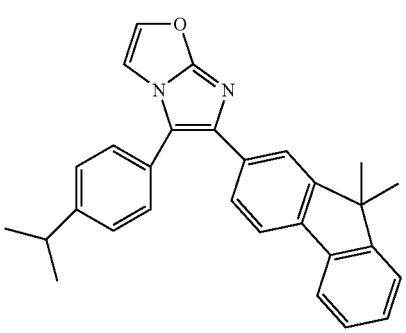

II-79
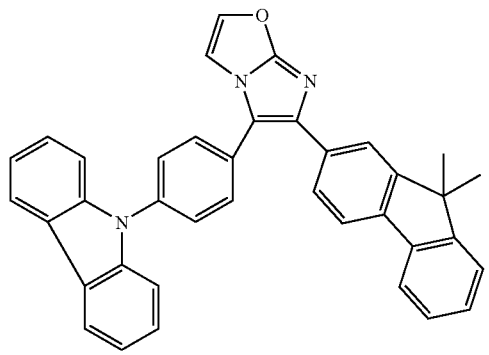
II-83
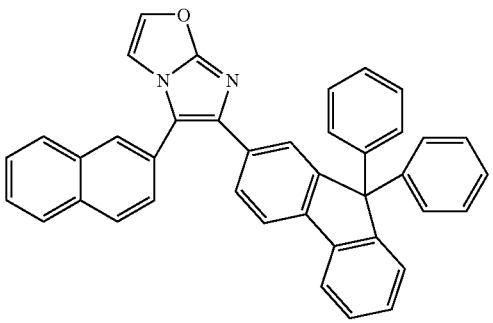
II-80
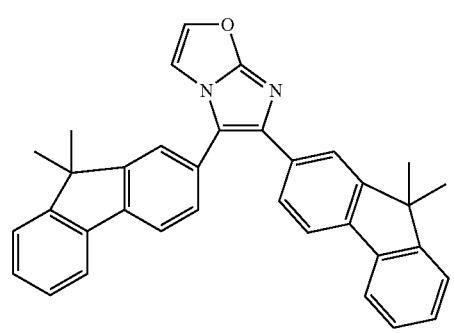
II-84
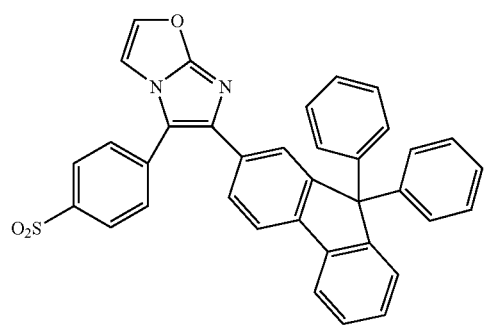
II-81
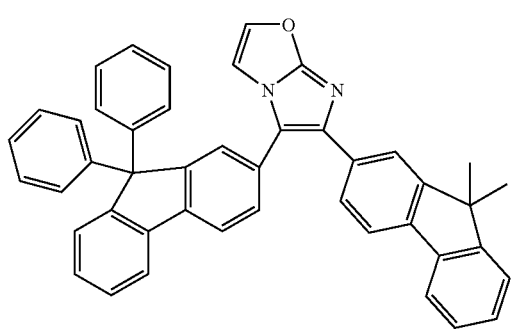
II-85
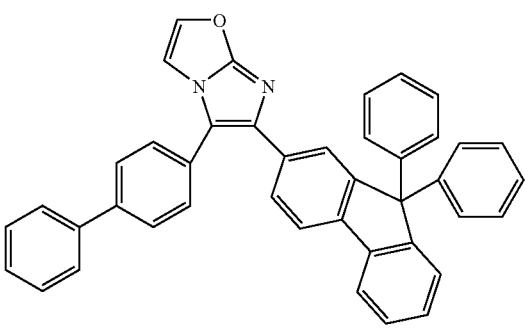
II-82
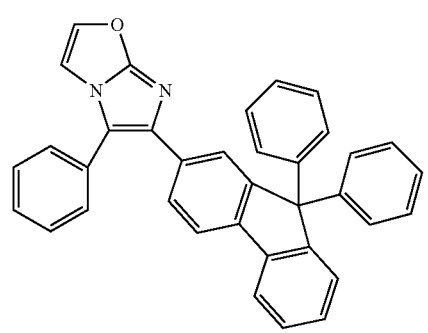
II-86
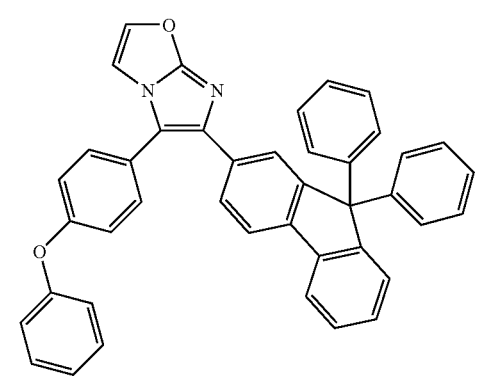

II-87
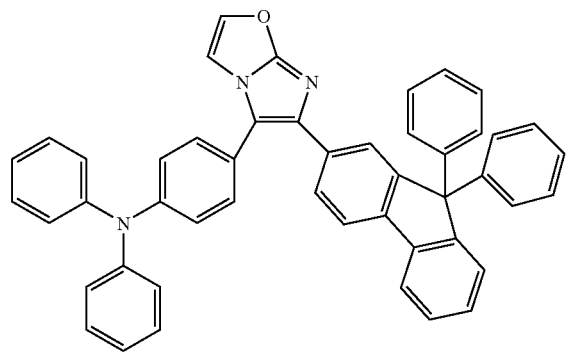
II-91
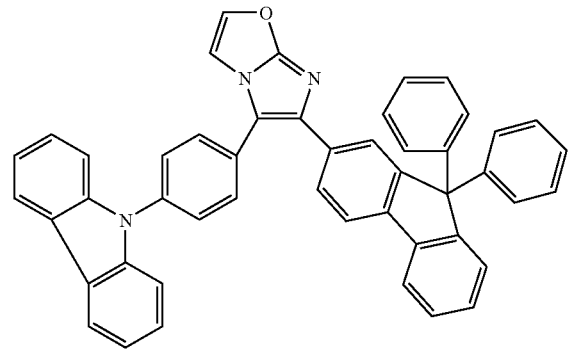
II-88
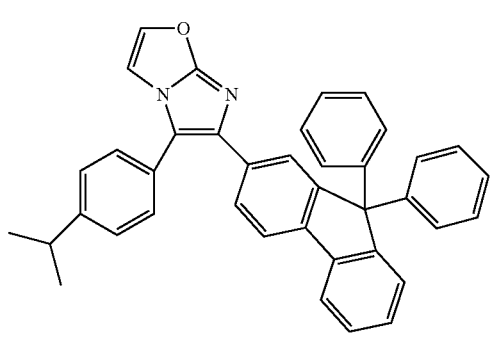
II-92
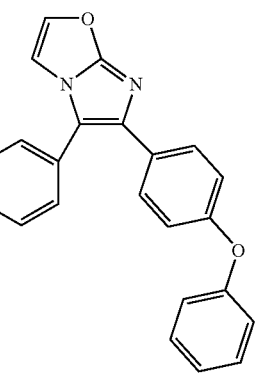
II-89
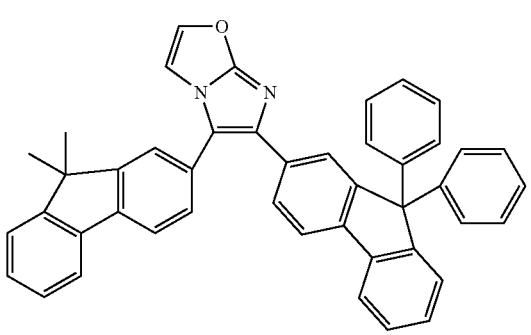
II-93
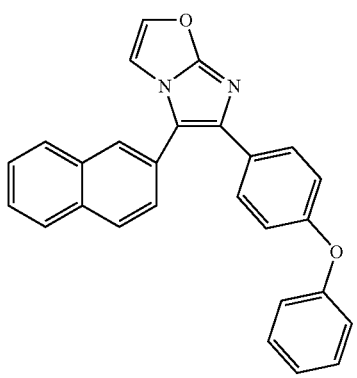
II-90
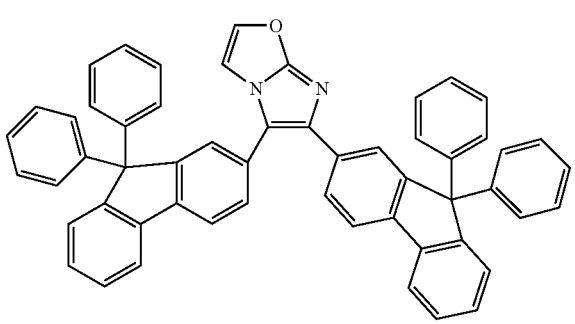
II-94
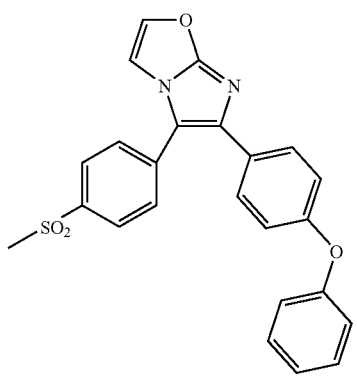

-continued
II-95
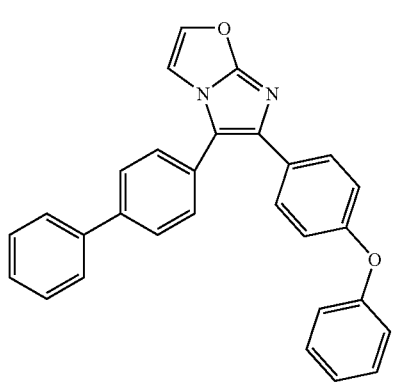
II-96
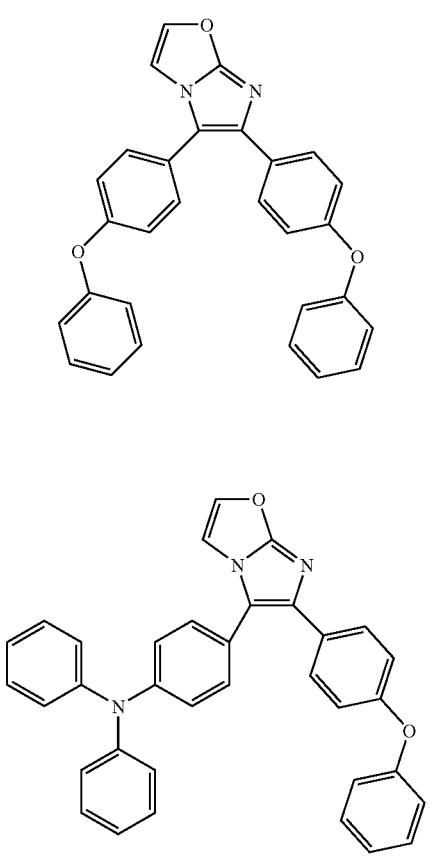
II-97
II-98
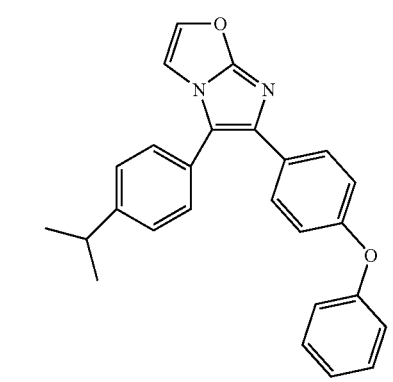
II-99
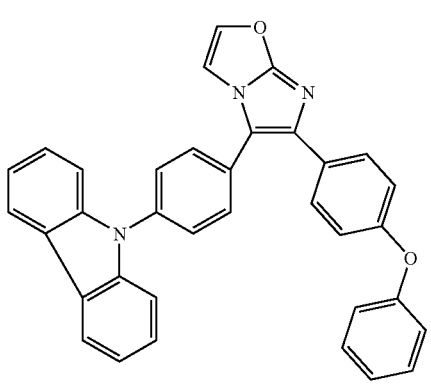
II-100
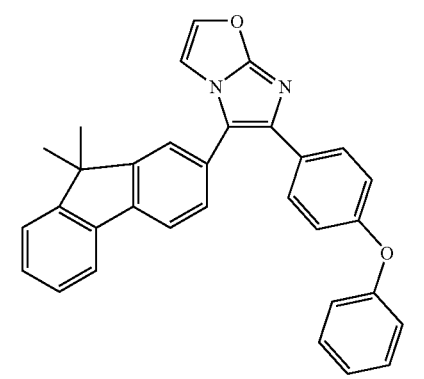
II-101
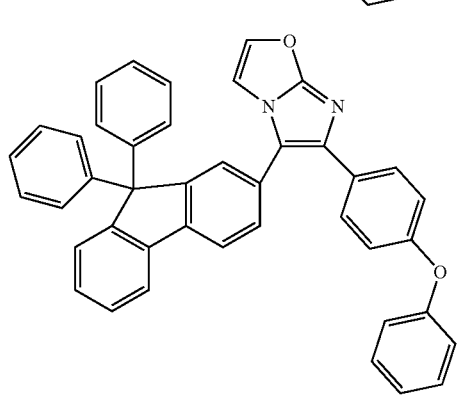
II-122
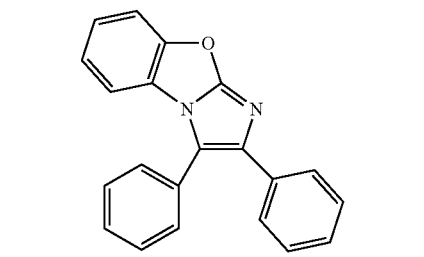
II-123
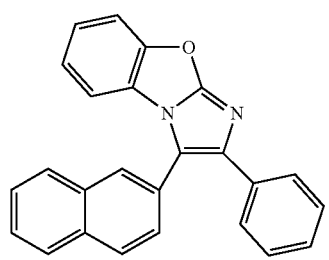

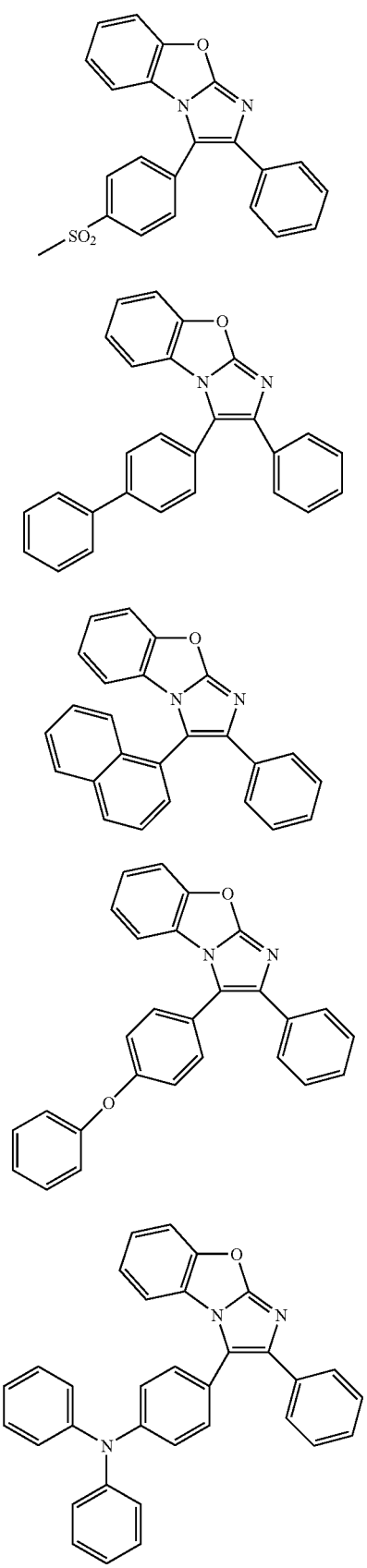
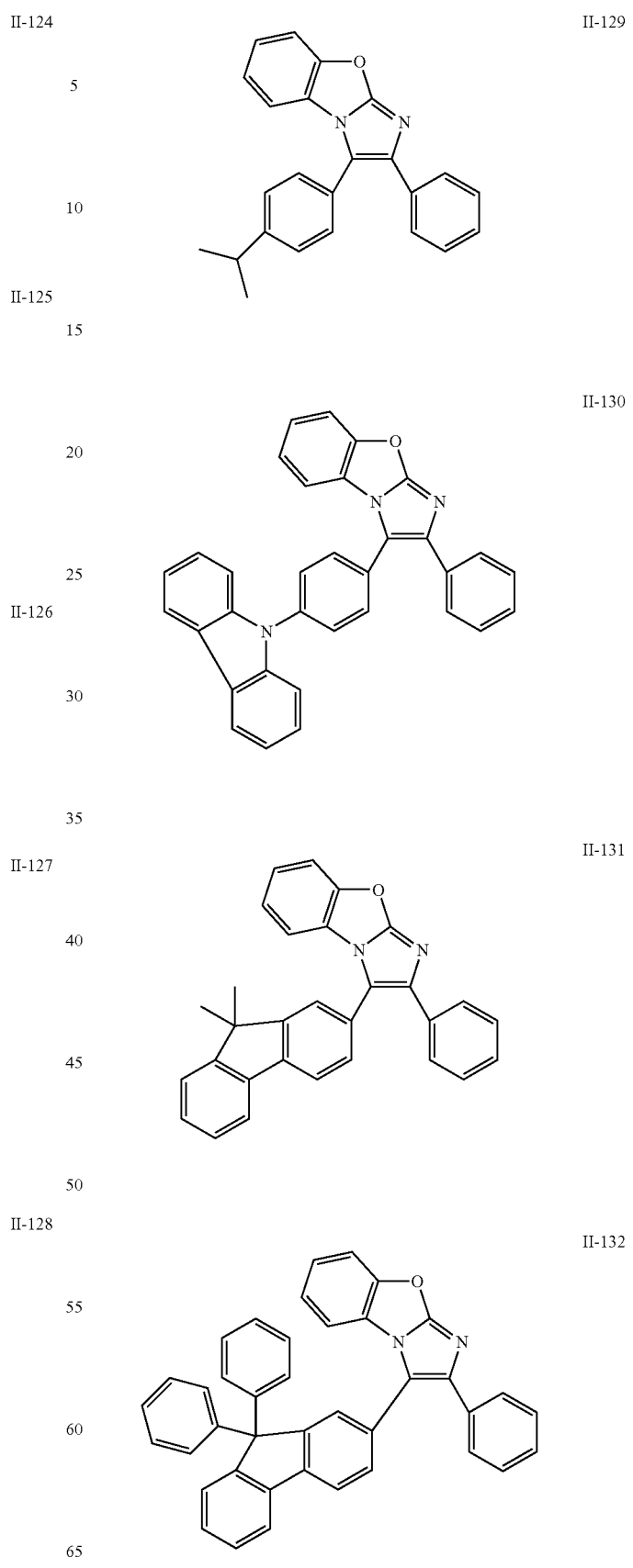

II-133
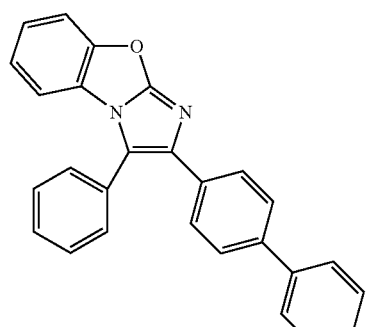
II-134
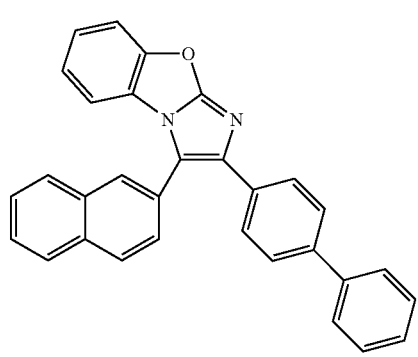
II-135
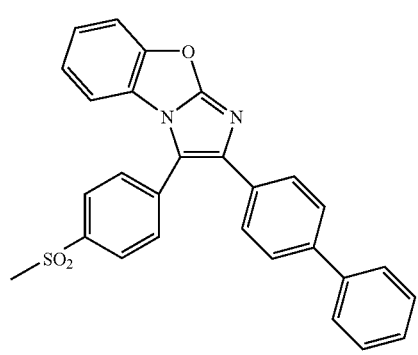
II-136
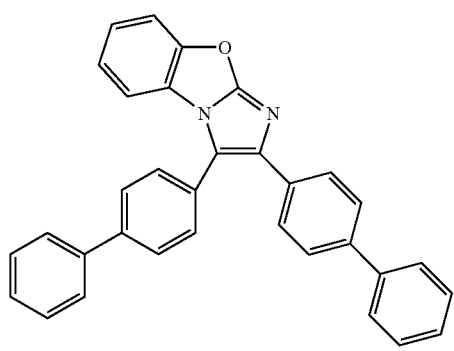
II-137
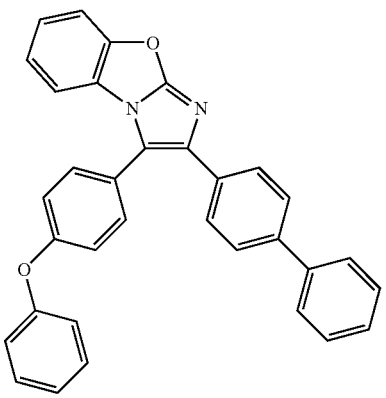
II-138
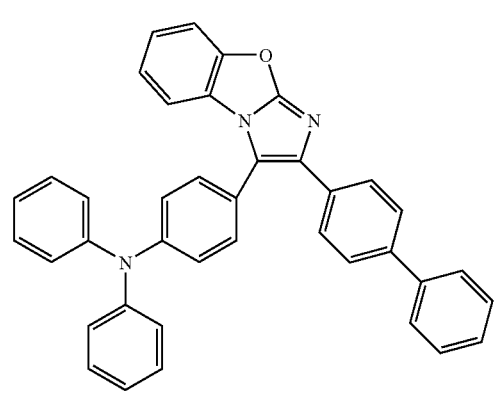
II-139
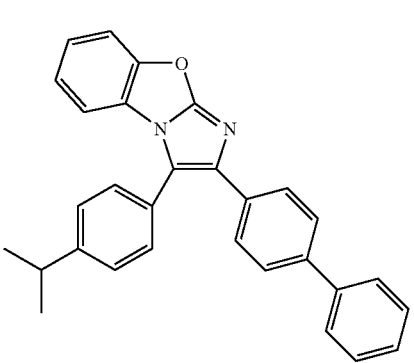
II-140
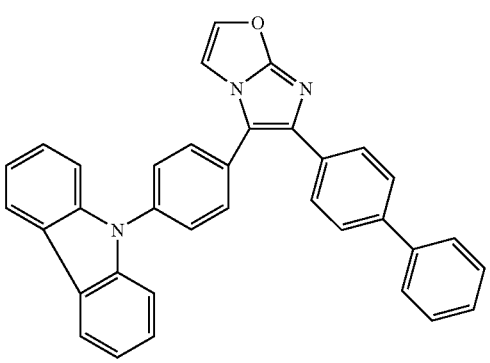

II-141
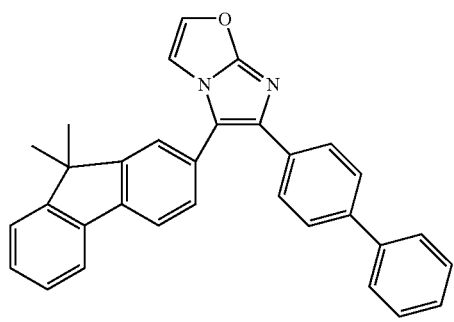
II-142
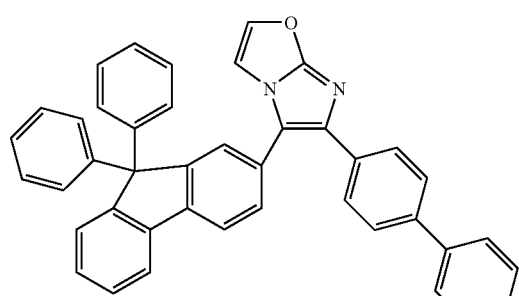
II-143
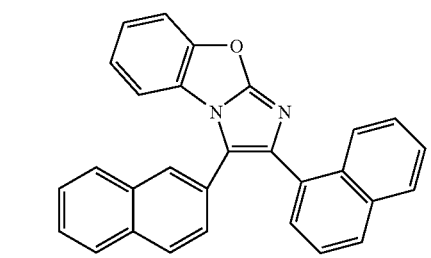
II-144
II-145
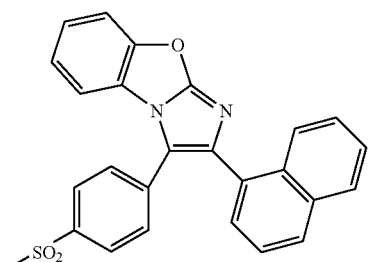
II-146
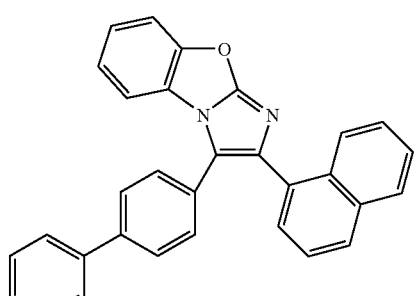
II-147
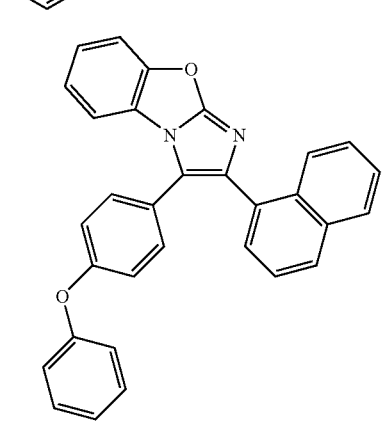
II-148
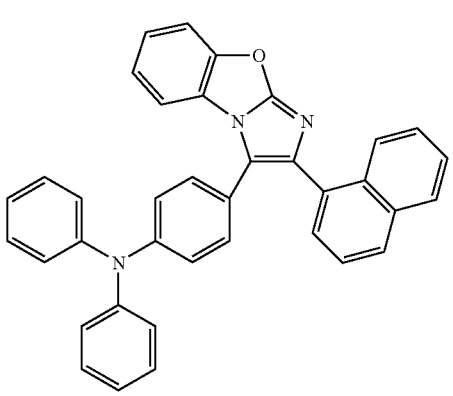
II-149
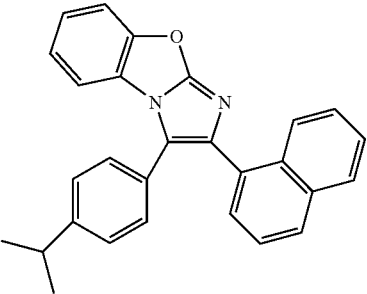

II-150
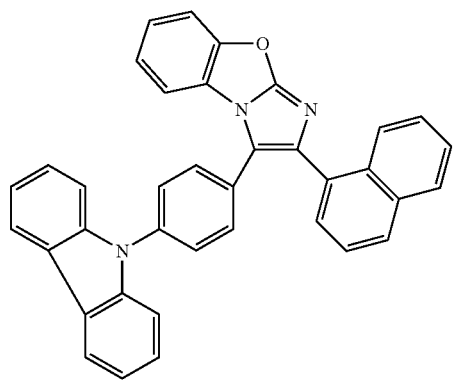
II-151
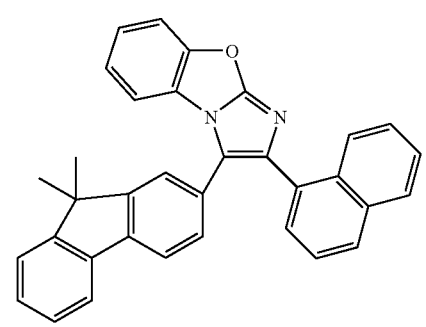
II-152
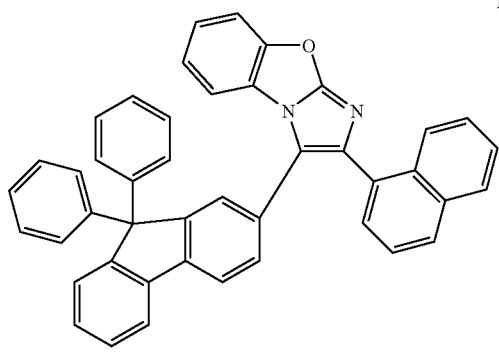
II-153
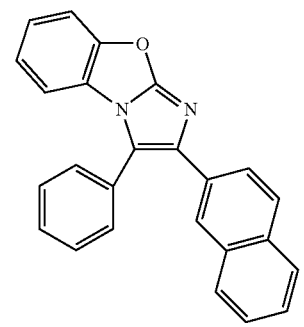
II-154
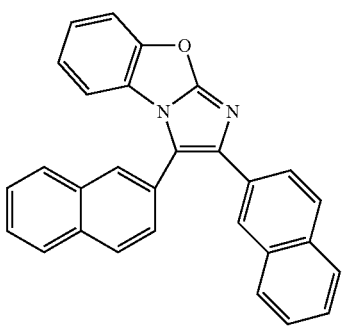
II-155
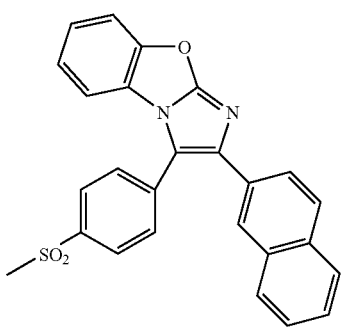
II-156
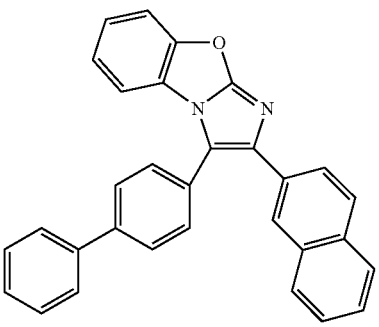
II-157
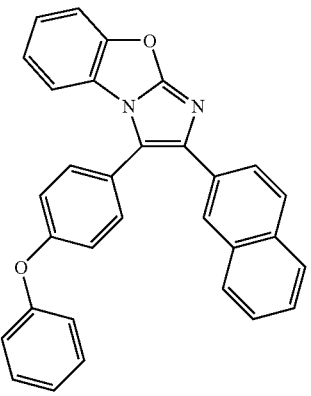

II-158
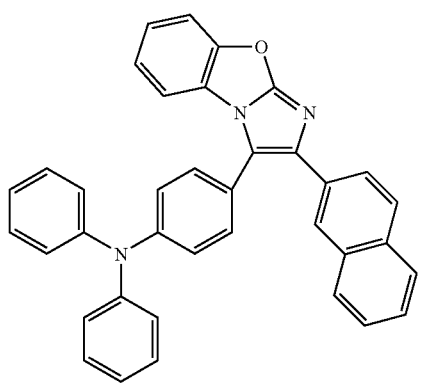
II-159
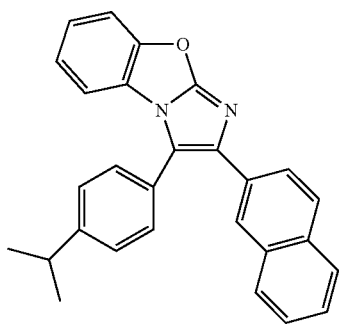
II-181
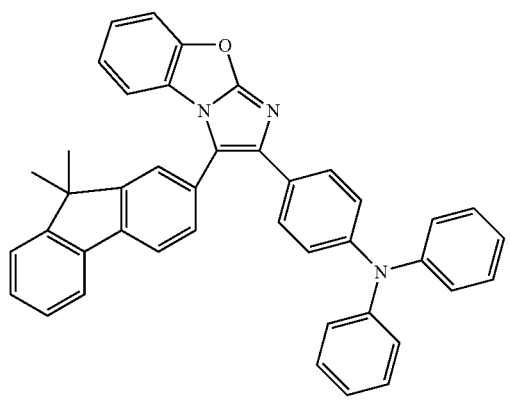
II-193
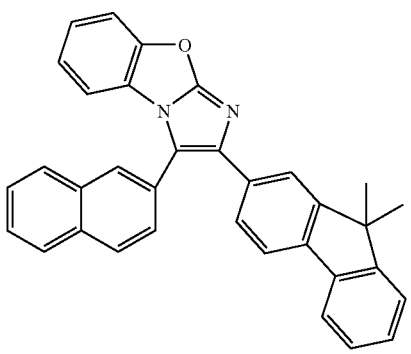
II-194
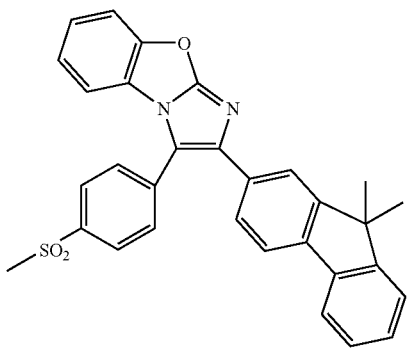
II-195
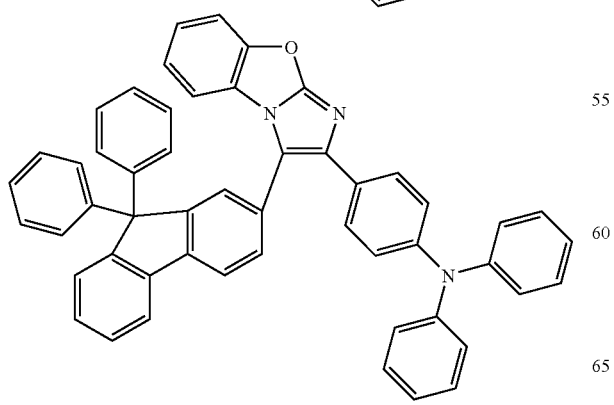
II-196
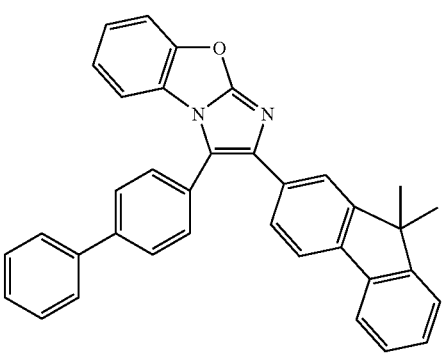

II-197
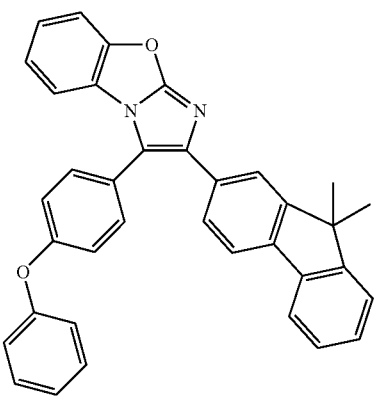
II-198
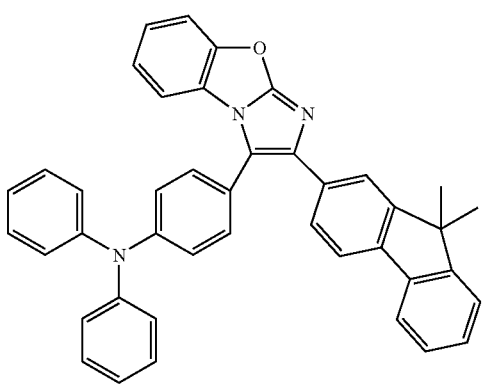
II-199
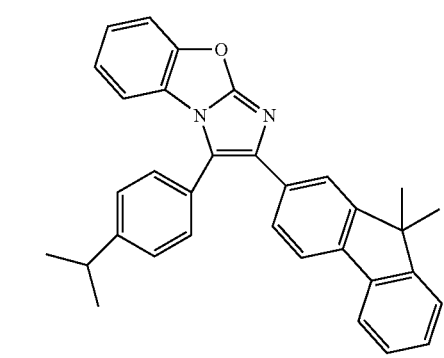
II-200
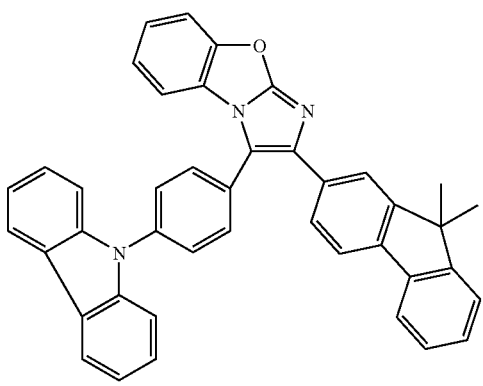
II-201
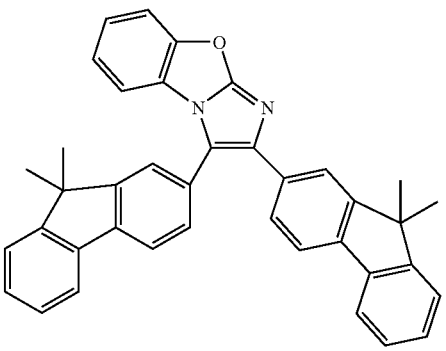
II-202
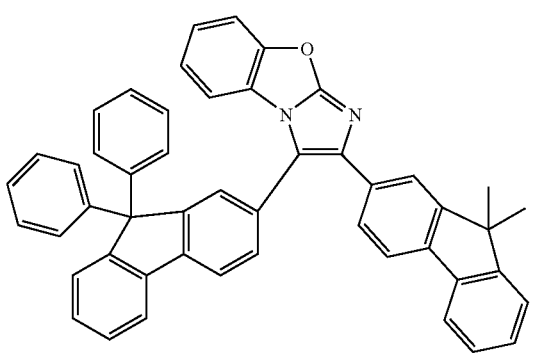
II-203
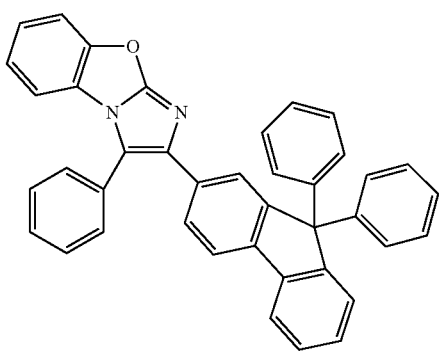
II-204
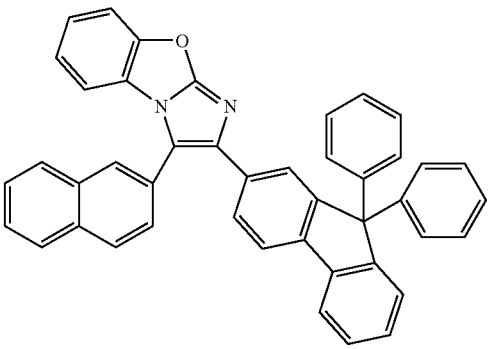

II-205
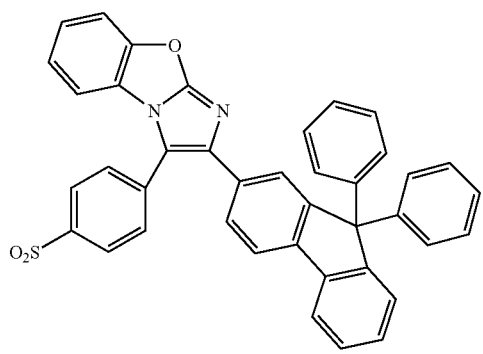
II-209
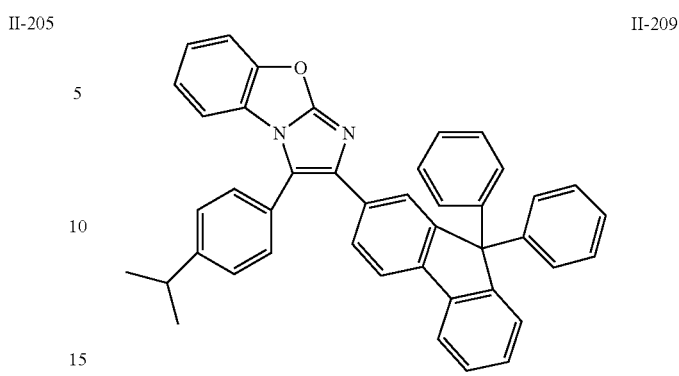
II-206
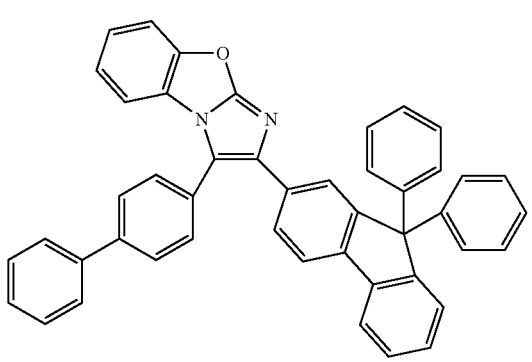
II-210
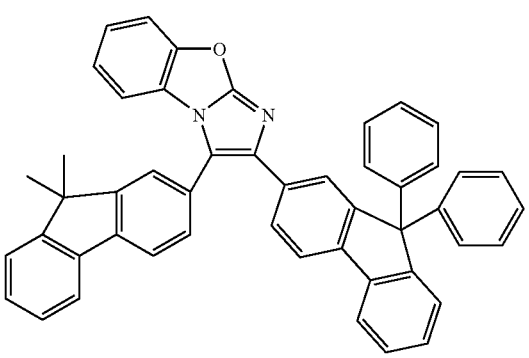
II-207
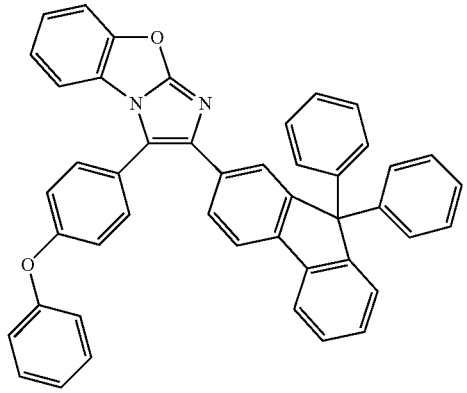
II-211
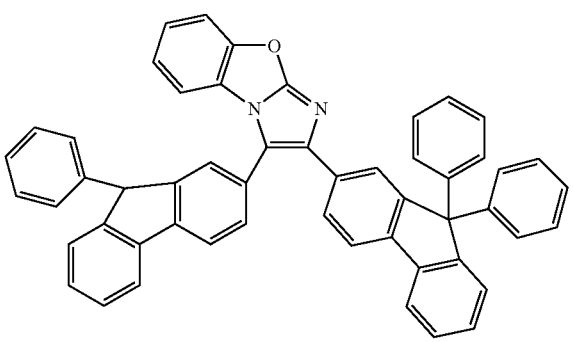
II-208
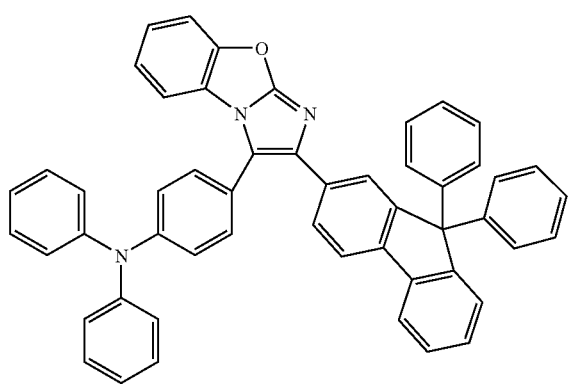
II-212
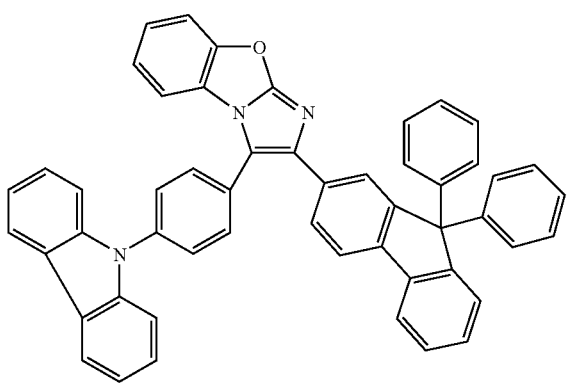

II-213
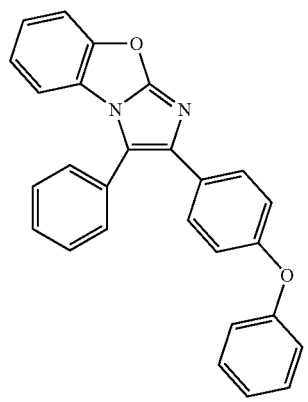
II-217
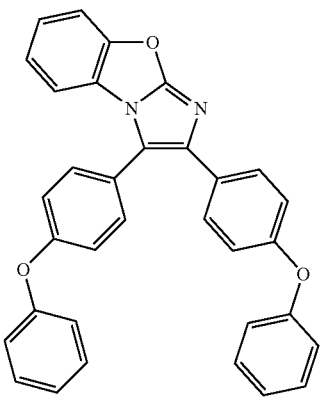
II-214
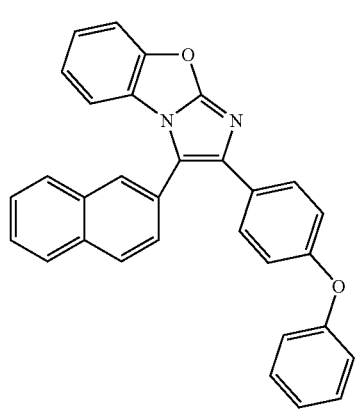
II-218
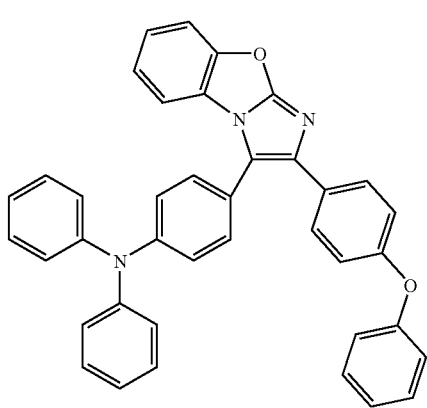
II-215
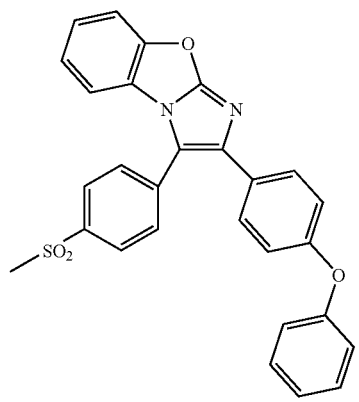
II-219
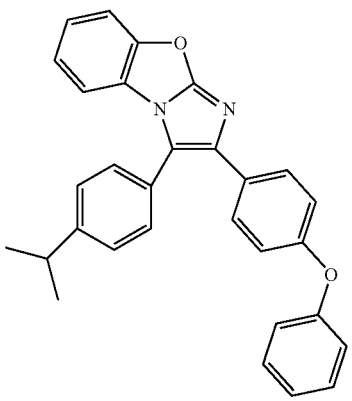
II-216
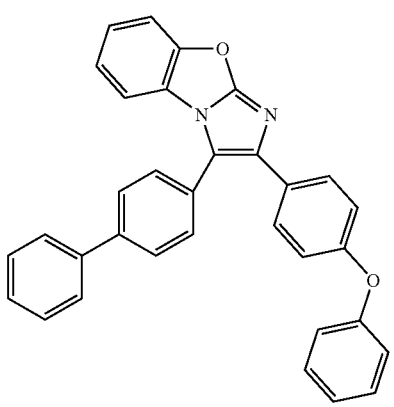
II-220
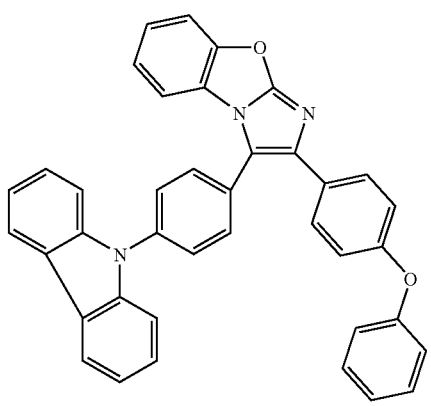

II-221
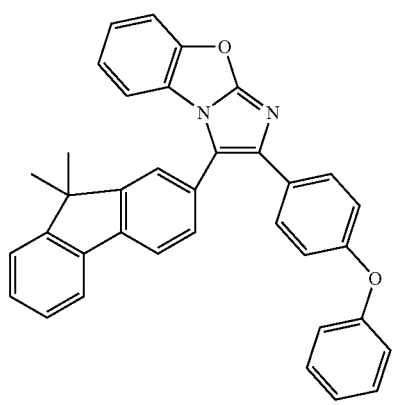
III-182
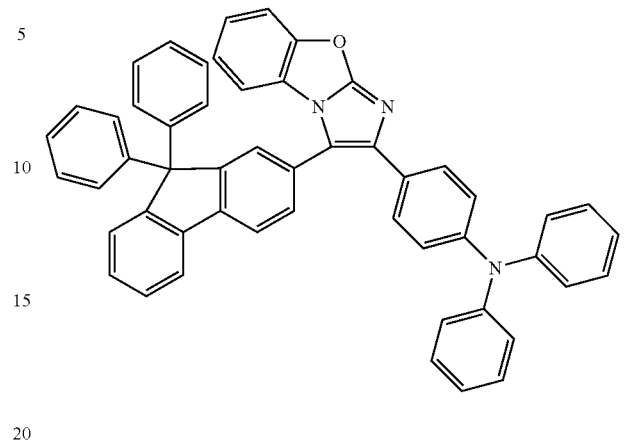
II-222
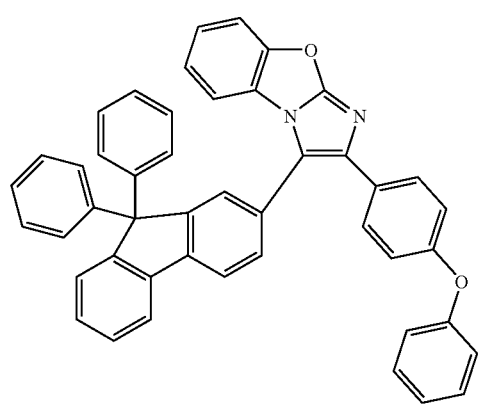
III-183
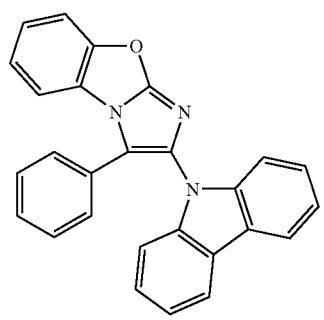
III-184
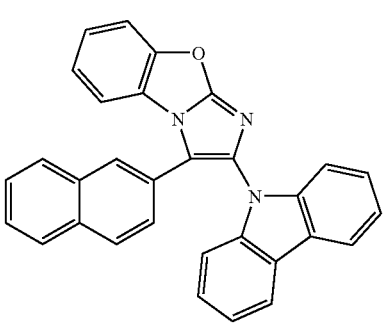
In a further embodiment, examples of the compound of Formula (3) above may not limited to, the compounds as illustrated below.
III-181
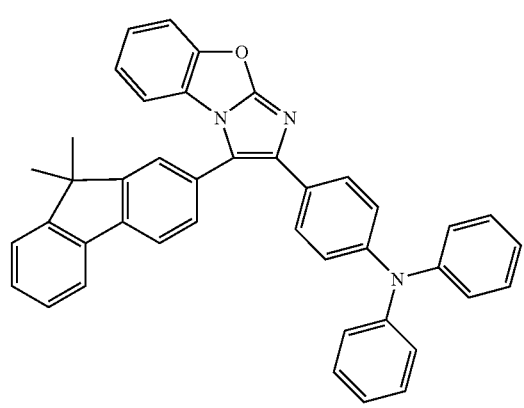
III-185
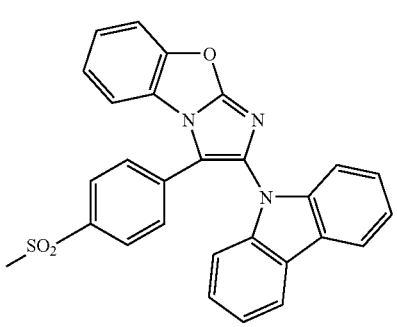

-continued
III-186
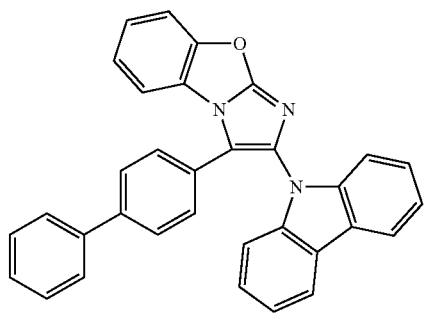
III-187
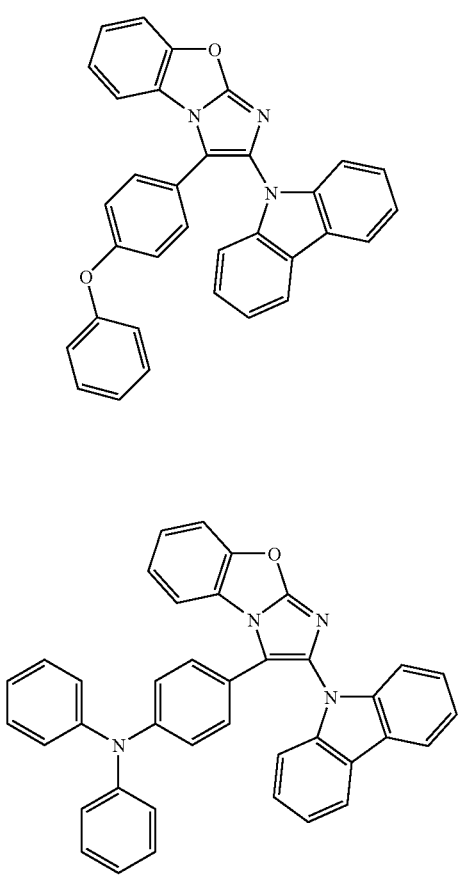
III-188
III-189
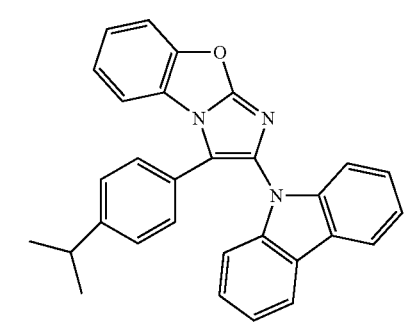
-continued
III-190
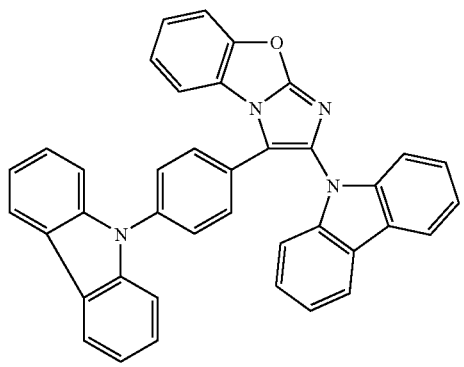
III-191
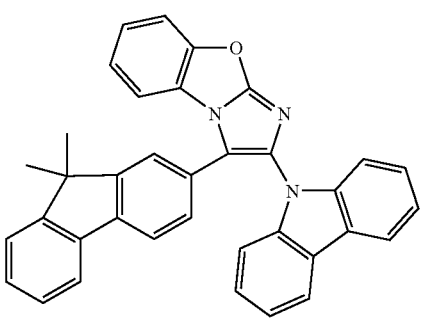
III-192
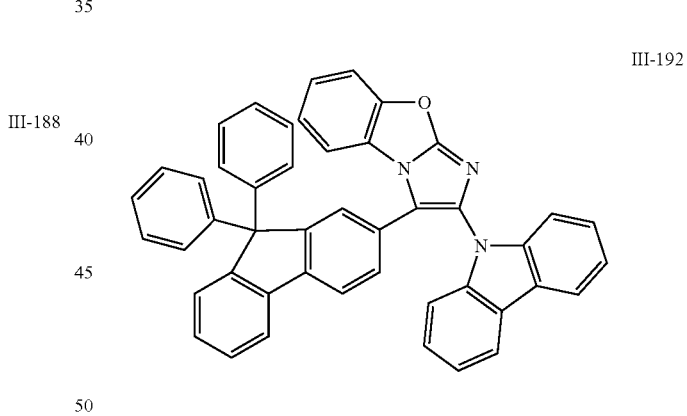
Moreover, examples of the compound of Formula (4) above may include, but are not limited to, the compounds as represented below.
IV-102
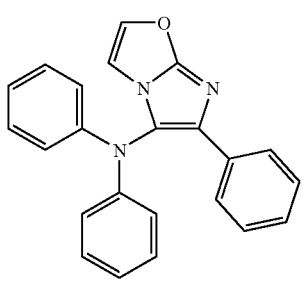

-continued
IV-103
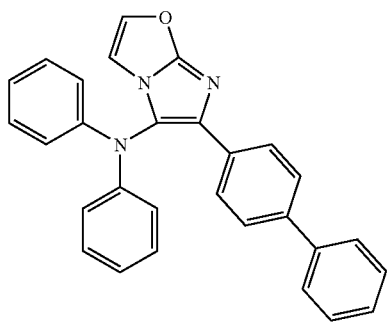
IV-104
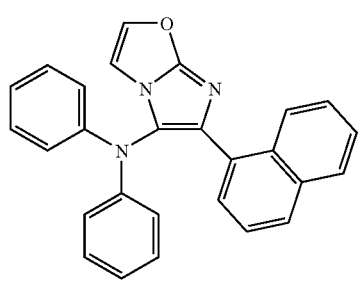
IV-105
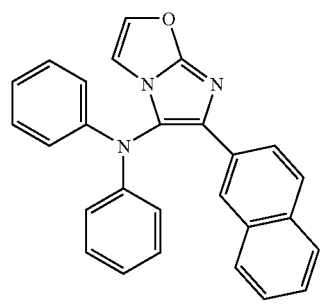
IV-106
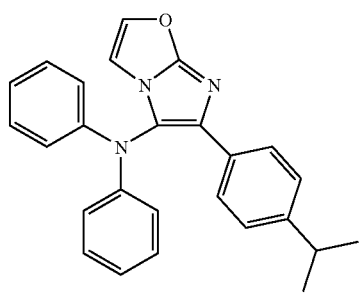
IV-107
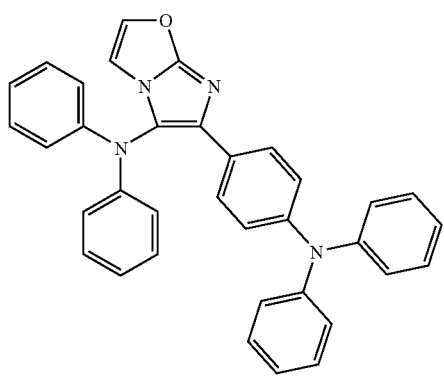
-continued
IV-109
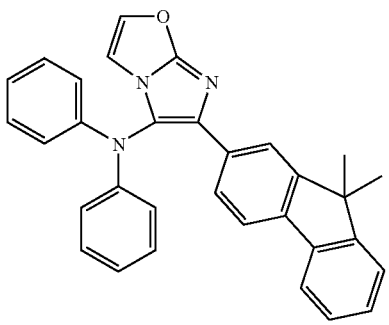
IV-110
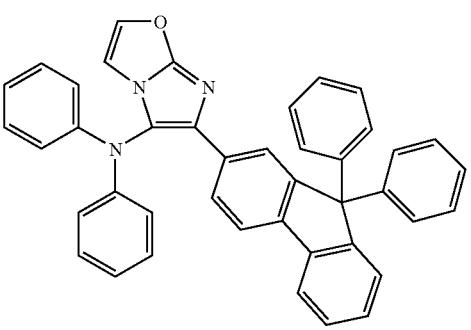
IV-111
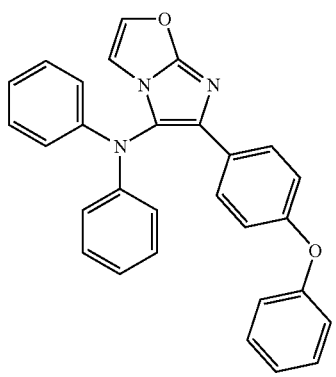
IV-223
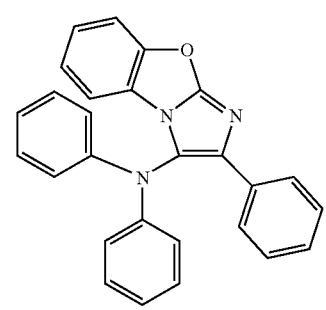

-continued
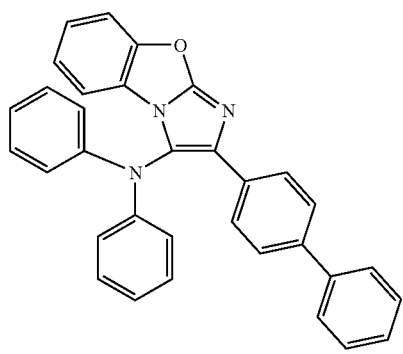
IV-224
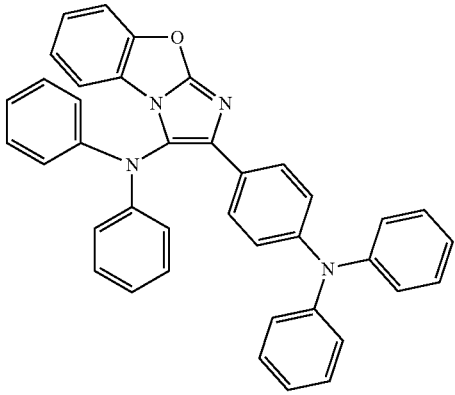
IV-228
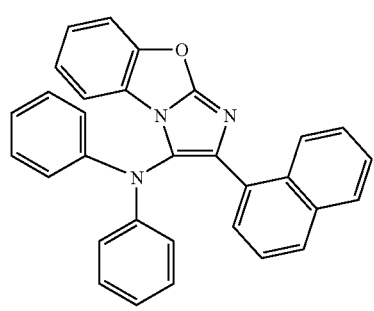
IV-225
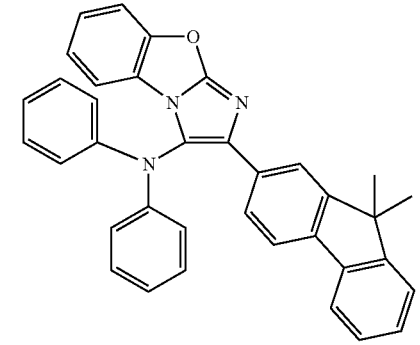
IV-230
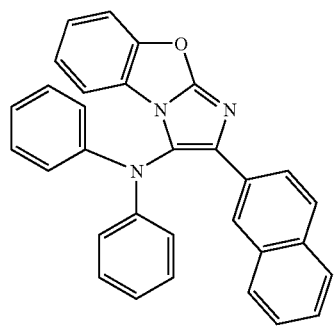
IV-226
IV-231
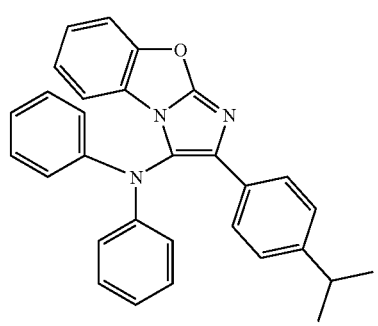
IV-227
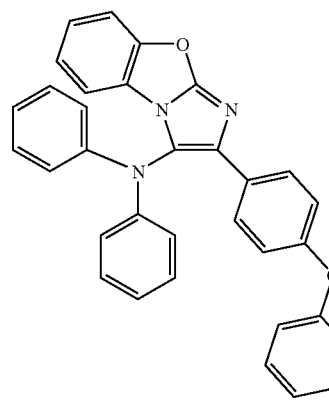
IV-232

Examples of the compound of Formula (5) above may include, but are not limited to, the compounds shown below.
V-108
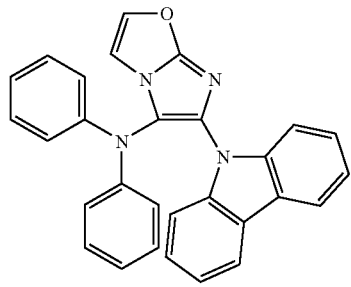
V-229
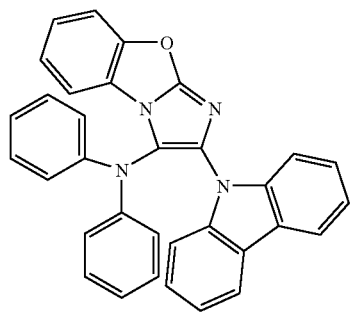
Additionally, examples of the compound of Formula (6) above may include, but to, the compounds below.
VI-112
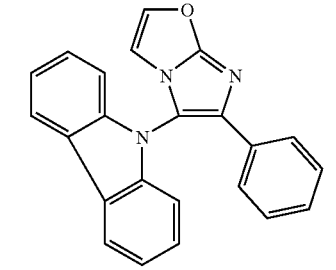
VI-113
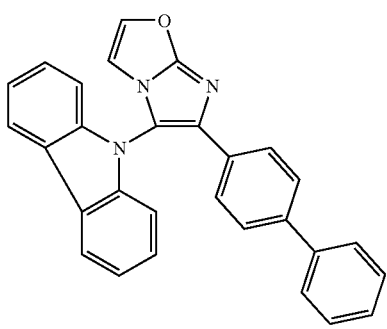
VI-114
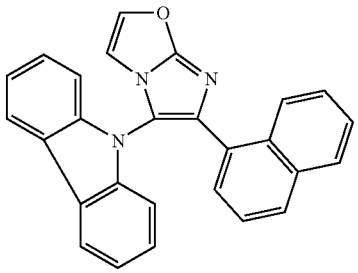
VI-115
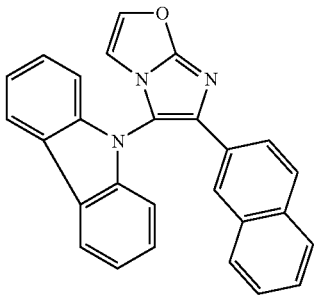
VI-116
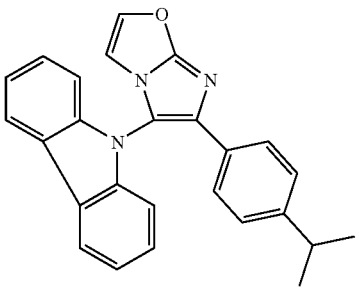
VI-117
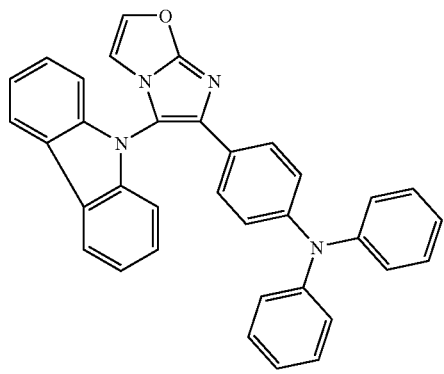
VI-119
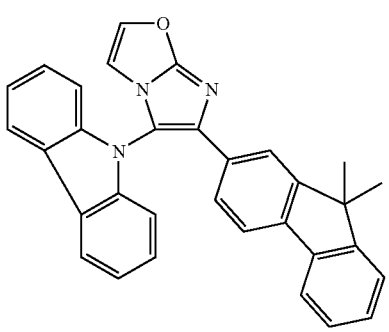

-continued
VI-120
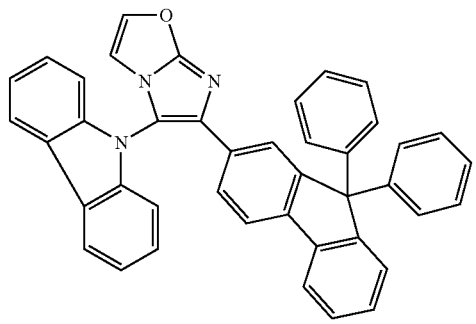
VI-121
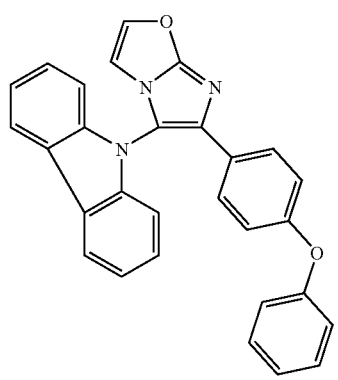
VI-233
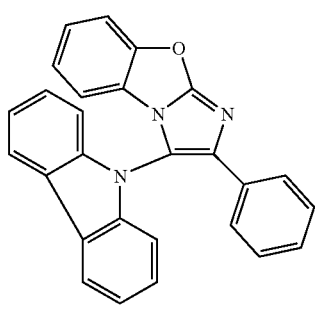
VI-234
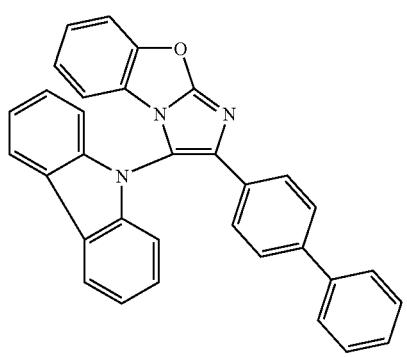
-continued
VI-235
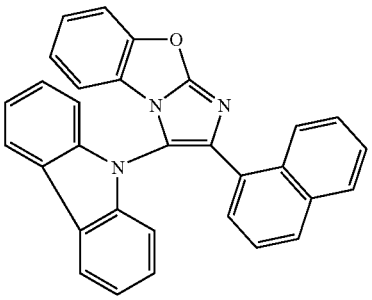
VI-236
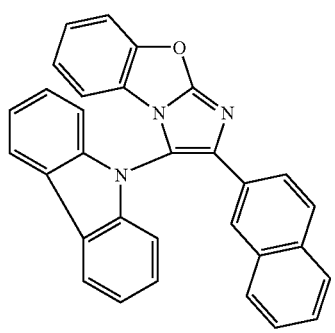
VI-237
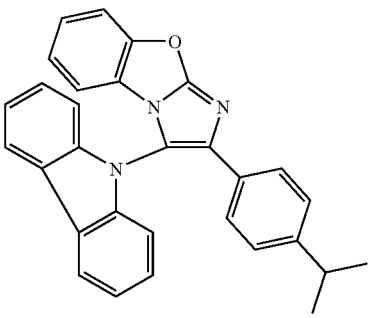
VI-238
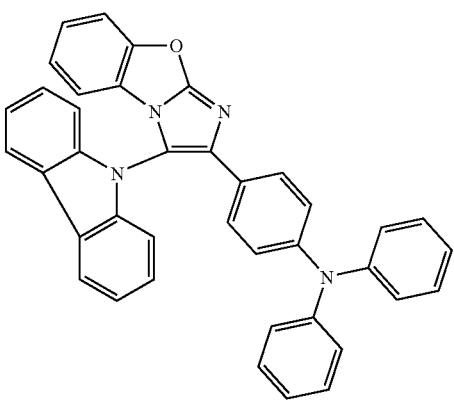

-continued
VI-240
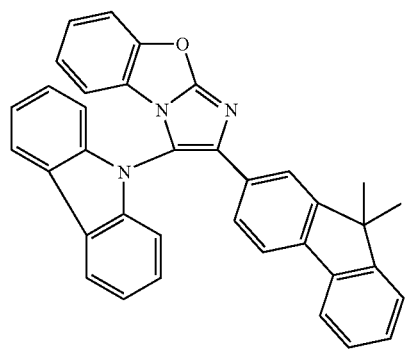
VI-241
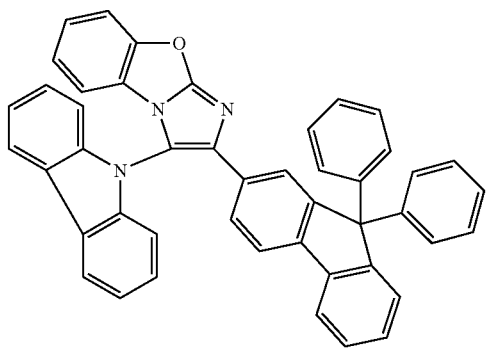
VI-242
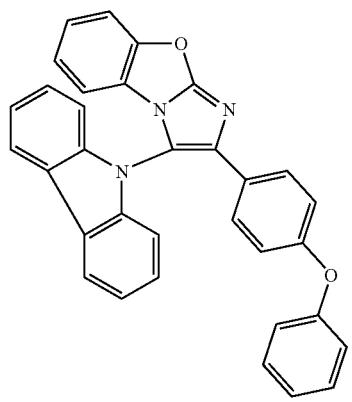
In another embodiment, examples of the compound of Formula (7) above may include, but are not limited to, the compounds illustrated below.
VII-118
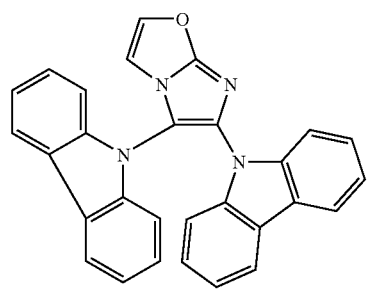
-continued
VII-239
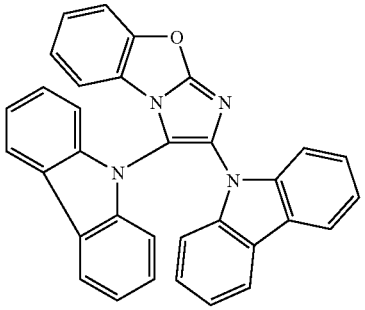
Furthermore, examples of the compound of Formula (8) above may include, but are not limited to, the compounds below.
VIII-1
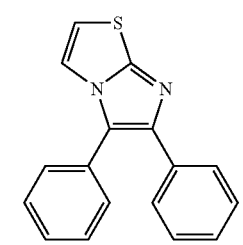
VIII-2
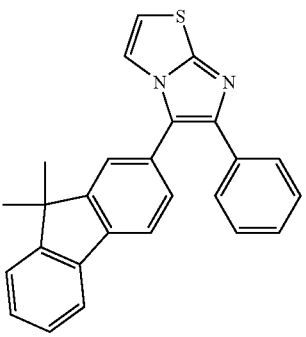
VIII-3
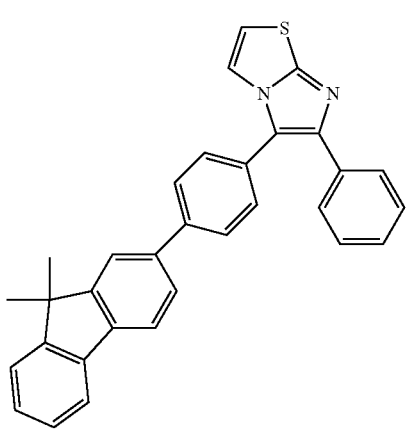

-continued
VIII-5
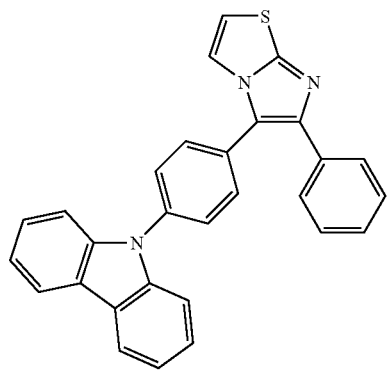
VIII-7
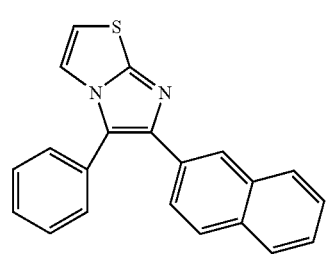
VIII-8
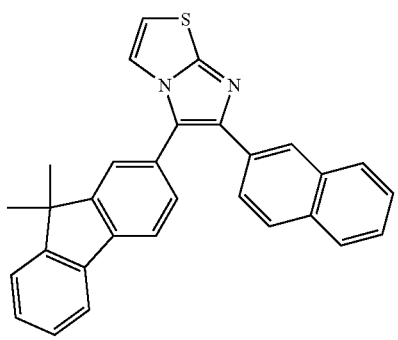
VIII-9
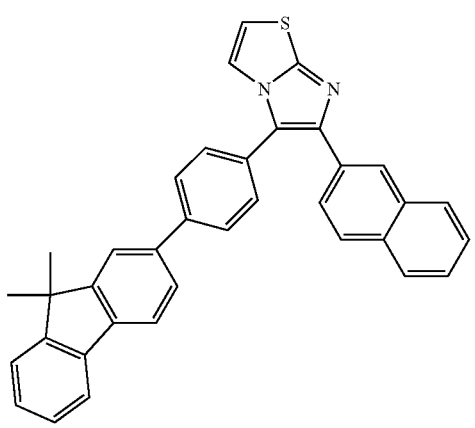
-continued
VIII-11
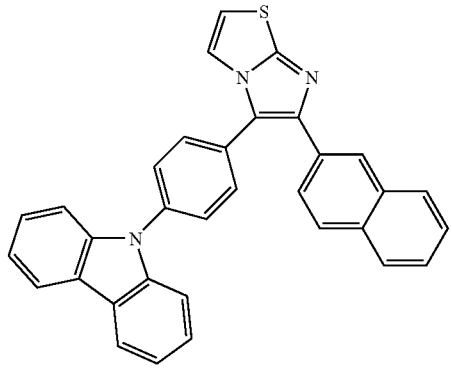
VIII-13
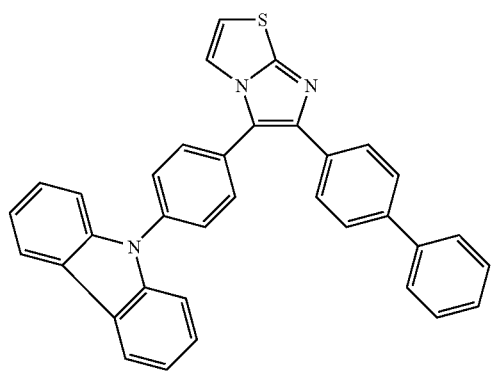
VIII-14
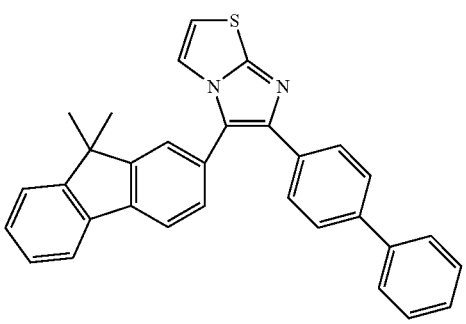
VIII-17
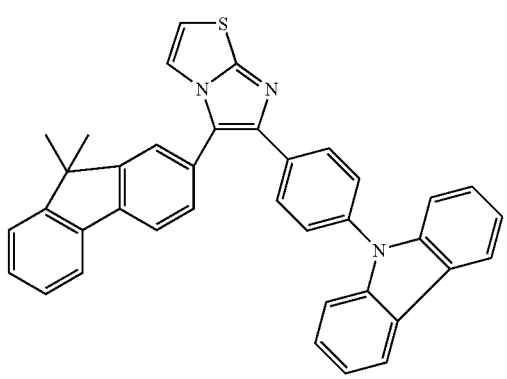

-continued
VII-18
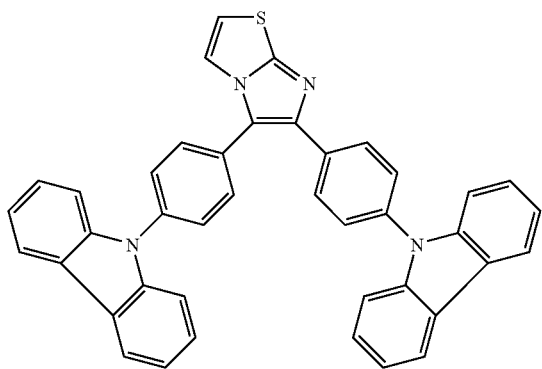
VIII-20
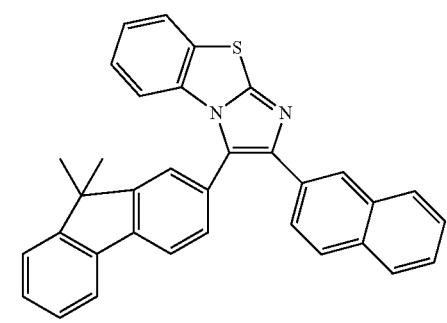
VIII-21
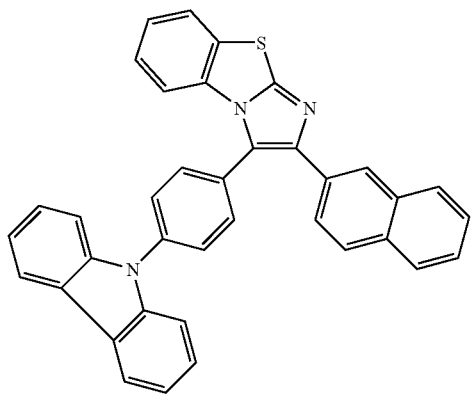
VIII-23
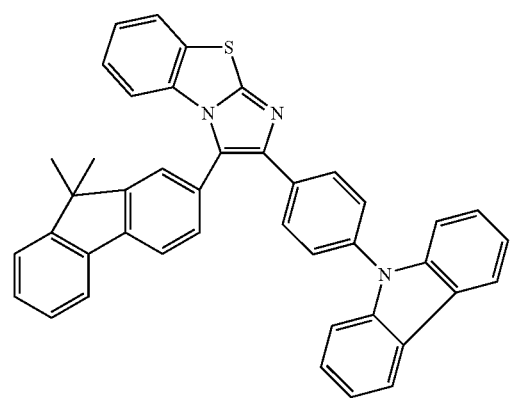
Examples of the compound of Formula (9) above may include, but are not limited to, the compounds depicted below.
IX-4
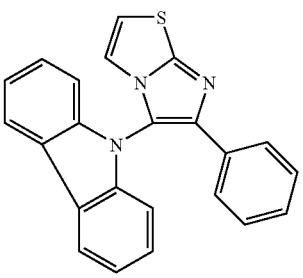
IX-10
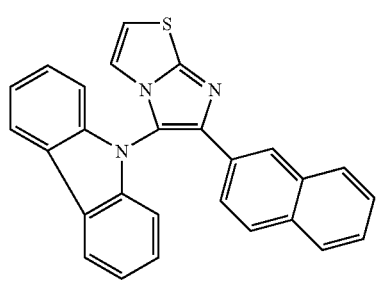
IX-12
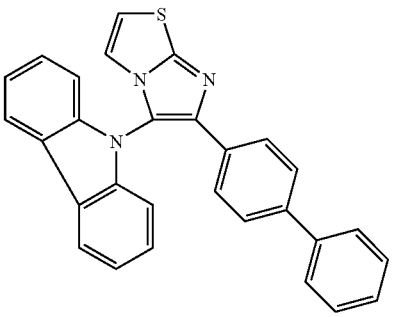
IX-16
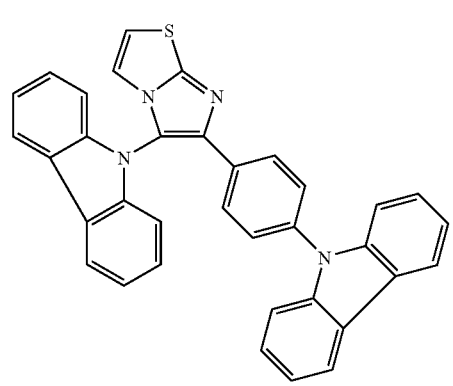

-continued
IX-19
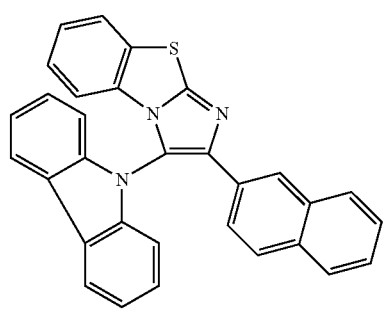
IX-22
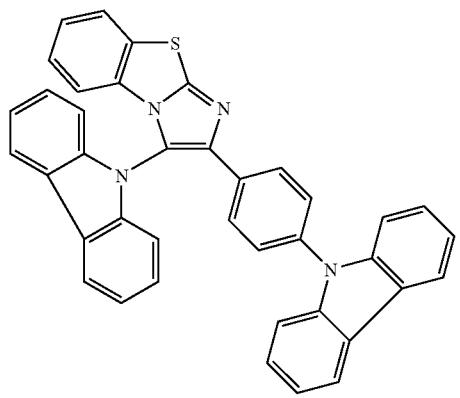
Examples of the compound of Formula (10) above may include, but are not limited to, the compounds illustrated below.
X-6
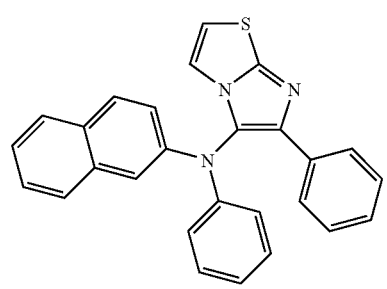
X-15
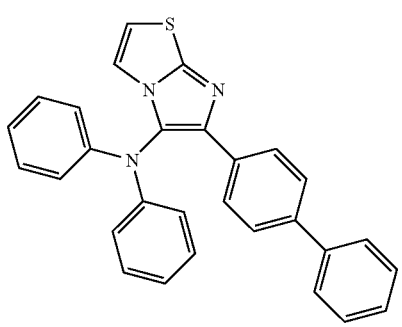
Examples of the compound of Formula (11) above may include, but are not limited to, the compounds shown below.
XI-1
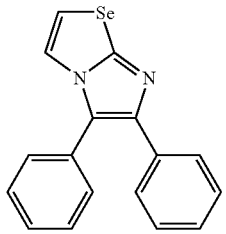
XI-2
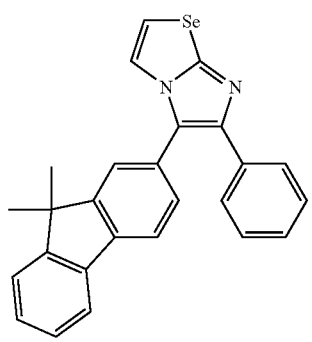
XI-5
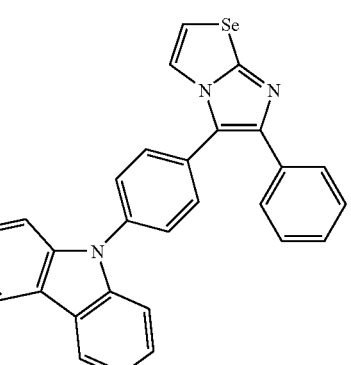
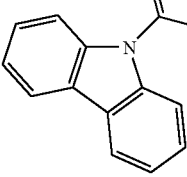
XI-7
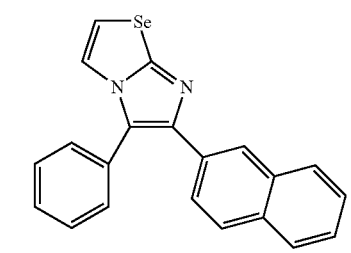
XI-8
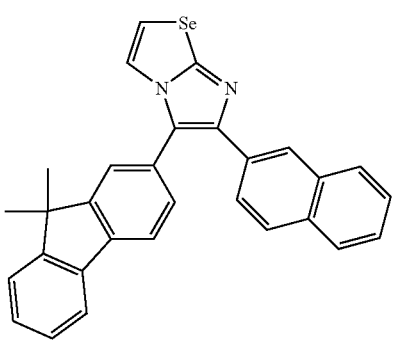

-continued
XI-9
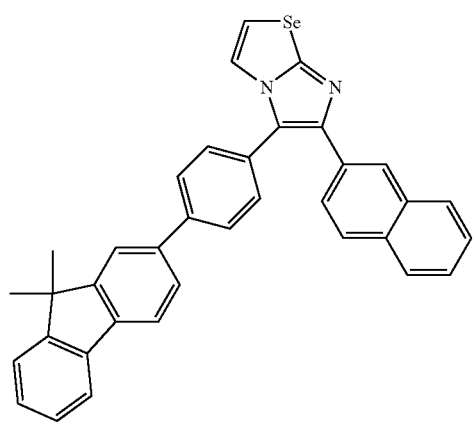
XI-11
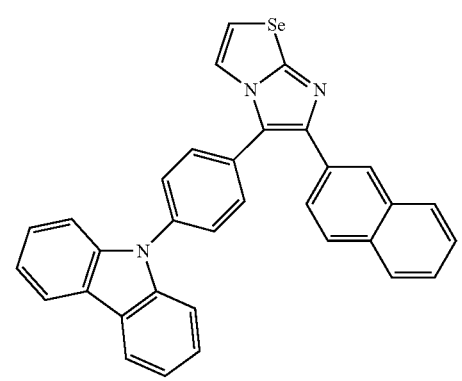
XI-13
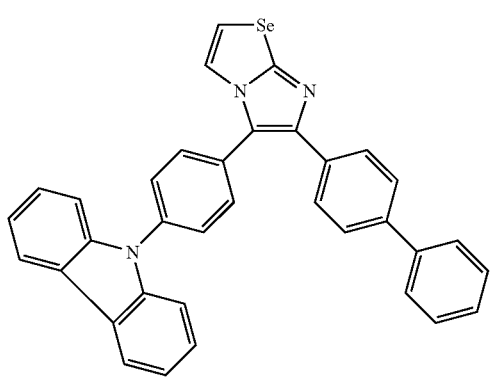
XI-14
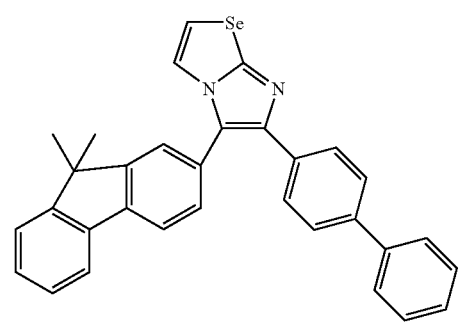
-continued
XI-17
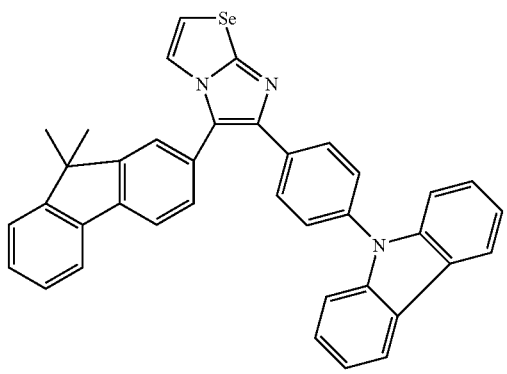
XI-18
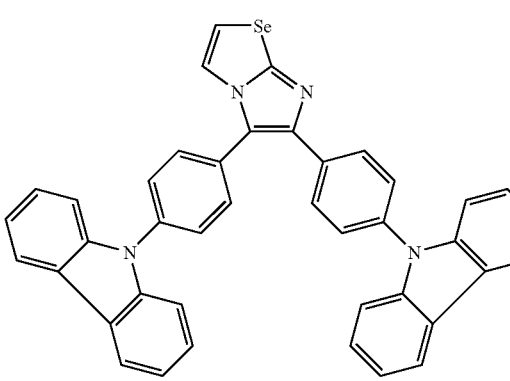
XI-20
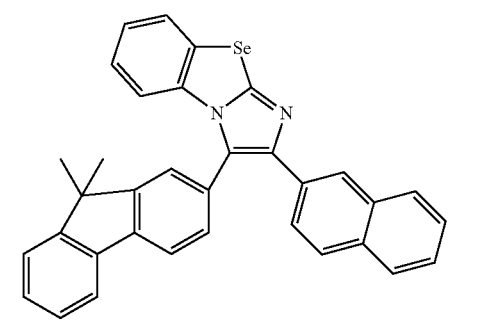
XI-21
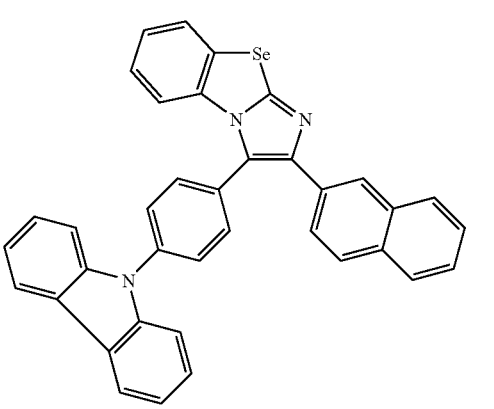

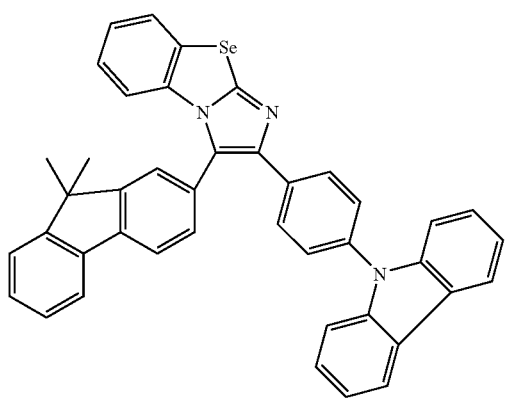
XI-23
Examples of the compound of Formula (12) above may include, but are not limited to, the compounds shown below.
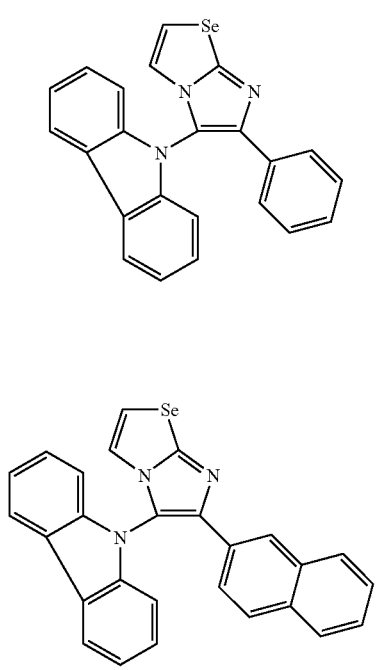
XII-4
XII-10
XII-12
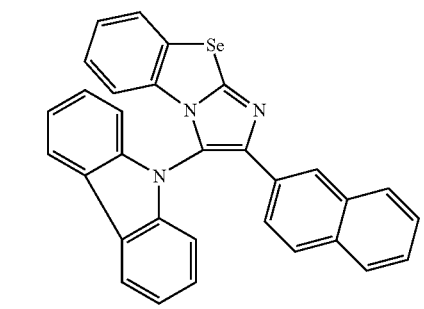
XII-16
XII-19
XII-22
Examples of the compound of Formula (13) above may include, but are not limited to, the compounds illustrated below.
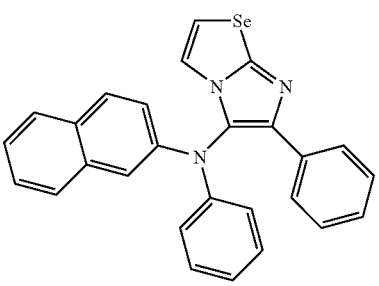
XIII-6

-continued

XIII-15

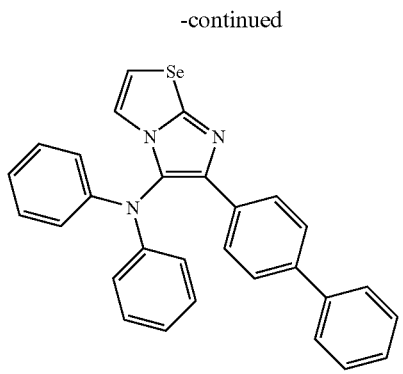

According to an embodiment of the present invention, the imidazole ring-containing compound of Formula (1) may have strong blue light emission and hole transporting characteristics and may be effectively used as a blue luminescent material and phosphorescent and fluorescent host materials. A method of manufacturing an organic EL display device using an organic film made of the imidazole ring-containing compound will be described below.

FIG. 1 is a sectional view illustrating a structure of a typical organic EL display device. As shown in FIG. 1, an anode may be formed by coating an anode material on a surface of a substrate. Any substrate that is commonly used for organic EL devices may be used. In particular, the substrate may be a glass substrate or a transparent plastic substrate because they are easy to handle, waterproof and have an even surface. Examples of anode materials may include indium tin oxide (ITO), indium zinc oxide (IZO), tin oxide ($SnO_2$), and zinc oxide (ZnO), which are transparent and have strong conductivity.

A hole injecting layer (HIL) may be formed by coating a HIL material on the anode using thermal vacuum deposition or spin coating. The HIL materials may include the Starbust type amine materials such as, CuPc, TCTA, m-MTDATA, and m-MTDAPB, as illustrated below, and not limited to thereof.

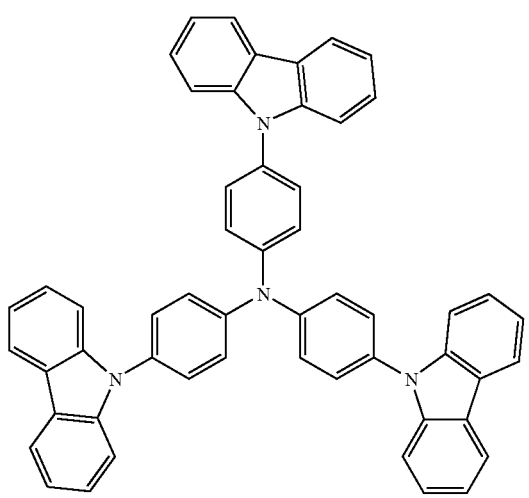

TCTA

-continued

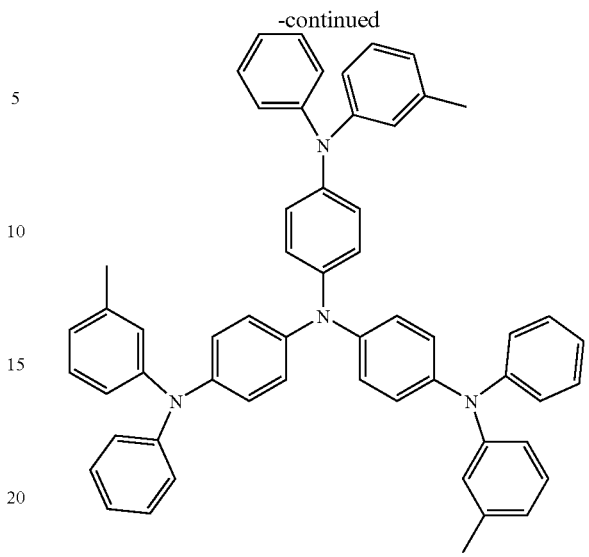

m-MTDATA

A hole transporting layer (HTL) may be formed by coating a HTL material on the HIL using thermal vacuum deposition or spin coating. Examples of HIL materials may include, but are not limited to, N,N'-bis(3-methylphenyl)-N,N'-diphenyl-[1,1-biphenyl]-4,4'-diamine (TPD), N,N'-di (naphthalene-1-yl)-N,N'-diphenyl benzidine (α-NPD).

An electroluminescent layer (EML) may be formed on the HTL. The EML may be made of any material, for example, the compound of Formula (1) alone or in combination with a dopant. In the latter case where the compound of Formula (1) acts as an emissive host, exemplary fluorescent dopants that may be used together include IDE102 and IDE105 (Idemitsu Co., Southfield, Mich.) and exemplary phosphorescent dopants that may be used together include $Ir(ppy)_3$ (green), where "ppy" is an abbreviation for phenylpyridine, $(4,6-F2\ ppy)_2Irpic$ (Adachi et al., 79 APPL. PHYS. LETT., 2082-2084 (2001)), and PtOEP (platinum(II) octaethylporphyrin. The EML may be fabricated using any method known in the art, for example, thermal vacuum co-deposition.

According to an embodiment, the amount of a dopant used may be in a range of about 0.1 parts to about 20 parts by weight, and in particular, about 0.5 parts to about 12 parts by weight, with respect to 100 parts by weight of the EML material (the amount of the compound of Formula (1) used as a host plus the amount of the dopant). If the amount of the dopant is less than 0.1 parts by weight, effects of adding the dopant are trivial. If the amount of the dopant is greater than 20 parts by weight, undesirable concentration quenching occurs in both phosphorescence and fluorescence.

An electron transporting layer (ETL) may be formed on the EML by any method known in the art, such as vacuum deposition or spin coating. A suitable material for the ETL includes, but is not limited to, Alq3. When the EML contains a phosphorescent dopant, a hole blocking layer (HBL) may be additionally formed on the EML by thermal vacuum deposition to prevent triplet excitons or holes from migrating into the ETL. Any material that can transport electrons and has a higher ionization potential than the emissive compound may be used for the HBL. Representative examples of HBL materials may include, but are not limited to, Balq and BCP, as shown below.

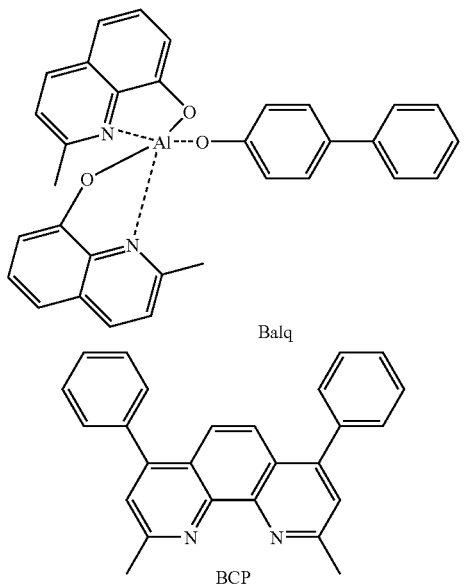

Balq

BCP

An electron injecting layer (EIL) may be optionally formed on the ETL. Examples of materials for the EIL include, but are not limited to, LiF, NaCl, CsF, $Li_2O$, and BaO. Next, a cathode may be formed by coating a metal on the EIL by thermal vacuum deposition thereby completing the manufacture of the organic EL device. Suitable metals for the cathode may include, but are not limited to Li, Mg, Al, Al—Li, Ca, Mg—In, and Mg—Ag. A transmittive cathode may be formed using, for example, ITO or IZO, to manufacture a front-emission device. An organic EL display device according to the present invention, which includes the anode, the HIL, the HTL, the EML, the HBL, the ETL, the EIL, and the cathode, may have an additional single or dual intermediate layer if required.

The present invention will be described in greater detail with reference to the following examples. The following examples are for illustrative purposes and are not intended to limit the scope of the invention.

EXAMPLES

Specific Example 1

Synthesis of compound (VIII-2)

Compound (VIII-2) was synthesized according to Reaction scheme (1) below.

Reaction Scheme 1

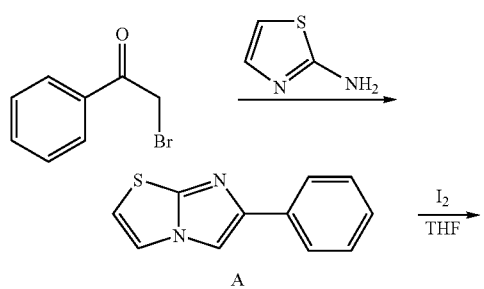

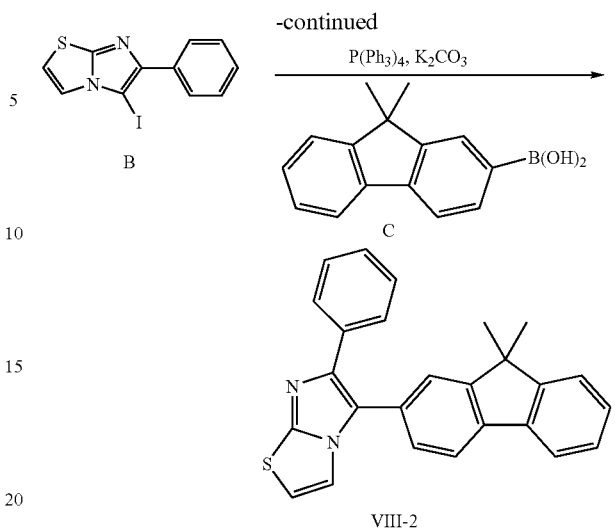

VIII-2

Synthesis of Intermediate (A)

6 g (50 mmol) of bromoacetophenone was dissolved in 250 ml of DME, and 10 g (50 mmol) of 2-aminothiazole in solid state was added to the solution, stirred for 5 hours at room temperature, and refluxed for 12 hours. The reaction product was distilled in a reduced pressure to remove the solvent, and 250 ml of dichloromethane was added to dissolve the remaining product. The pH of the solution was adjusted to pH 10 using a 10% sodium carbonate solution to separate the dichloromethane phase. The remaining aqueous phase was extracted twice using 200 ml of dichloromethane. The collected organic phase was dried using magnesium sulfate and the solvent evaporated from the dried product, and the resulting product was purified by silica gel column chromatography to obtain 8.4 g of intermediate (A) with a yield of 84%.

Synthesis of Intermediate (B)

1 g of intermediate (A) was dissolved in 15 ml of pyridine, and 1.9 g (7.5 mmol) of iodine was added thereto and stirred for 5 hours at 50° C. A saturated oxalic acid solution was added to stop the reaction, and extraction was performed three times using 20 ml of dichloromethane. The collected organic phase was dried using magnesium sulfate and the solvent evaporated from the dried product. The resulting product was purified by silica gel column chromatography to obtain 1.1 g of intermediate (B) with a yield of 73%.

The compound was characterized using proton NMR as follows: $^1H$ NMR ($CDCl_3$, 400 MHz) δ (ppm) 8.00 (d, 2H), 7.47-7.42 (m, 7H), 7.37-7.32 (m, 1H), 6.90 (s, 1H).

Synthesis of Intermediate (C)

1.63 g (6 mmol) of 2-bromo-9,9'-dimethylfluorene was dissolved in 20 ml of THF and 3.2 ml (7.8 mmol) of 2.5M n-butyl lithium dissolved in n-hexane butyl was added dropwise at −78° C. and stirred for 2 hours. 2 ml (18 mmol) of trimethyl borate was added to the reaction solution and stirred for 3 hours at the same temperature and further for 12 hours at room temperature. After adjusting the pH to pH 1 using an aqueous solution of 12M hydrochloric acid, the solution was stirred for 2 hours at room temperature. After adjusting the pH to pH 14 using a 4M NaOH solution, extraction was performed three times using 50 ml of diethyl ether each time. The collected organic phase was dried using magnesium sulfate and the solvent evaporated from the dried product. Then, the resulting product was purified by silica gel column chromatography to obtain 1 g of intermediate (C) in white solid form with a yield of 72%.

The compound was characterized using proton NMR as follows: $^1$H NMR (CDCl$_3$, 400 MHz) δ (ppm) 8.32 (s, 2H), 7.91-7.90 (m, 2H), 7.51 (s, 1H), 7.39 (s, 2H), 1.63 (s, 6H).

Synthesis of Compound (VIII-2)

90 mg (0.276 mmol) of intermediate (B) and 73 g (0.276 mmol) of intermediate (C) were dissolved in 3 ml of THF, and 7 mg (0.005 mmol) of tetrakistriphenylphosphine-palladium and a solution of 190 mg (1.38 mmol) of K$_2$CO$_3$ in 3 ml of distilled water were sequentially added and stirred at 75° C. for 12 hours. The reaction solution was extracted three times using 5 ml of ethyl acetate each time. The collected organic phase was dried using magnesium sulfate and the solvent evaporated from the dried product. Then, the resulting product was purified by silica gel column chromatography to obtain 100 mg of compound (VIII-1) with a yield of 95%.

The structure of this compound was identified by $^1$H NMR as follows: $^1$H NMR (CDCl$_3$, 400 MHz) δ (ppm) 7.80 (d, 1H), 7.75 (dd, 1H), 7.66 (dd, 2H), 7.48-7.42 (m, 4H), 7.37-7.34 (m, 2H), 7.27-7.21 (m, 3H), 6.84 (d, 1H), 1.44 (s, 6H).

Figure 2:
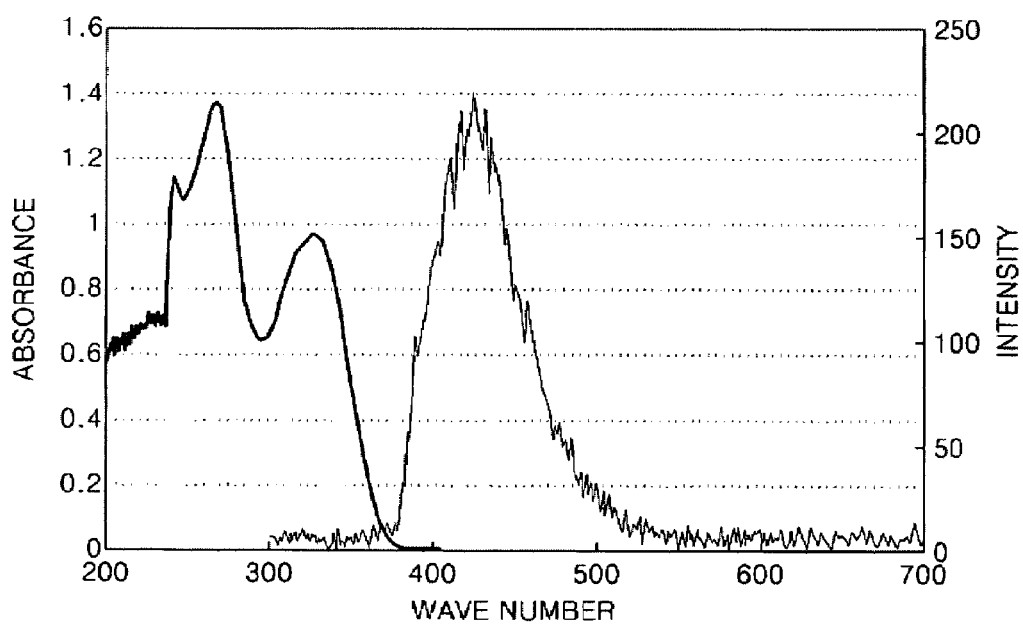
FIG. 2 is the UV spectrum and the photoluminescence (PL) spectrum of compound (VIII-2) according to the present invention.

Compound (VIII-2) obtained in Specific Example 1 was diluted to 0.2 mM using CHCl$_3$ for UV spectrum measurement. The results showed that compound (VIII-2) has a maximum absorption peak at 327.5 nm (FIG. 2).

Compound (VIII-2) was diluted to 10 mM using CHCl$_3$ to measure its PL characteristics. As a result, compound (VIII-2) has a maximum emission peak at 423 nm (FIG. 2). The color purity of the compound at this wavelength is CIE(x,y): 0.1959, 0.0907 in an NTSC chromaticity coordinate system.

Specific Example 2

Synthesis of Compound (VIII-3)

Compound (VIII-3) was synthesized according to Reaction scheme (2) below.

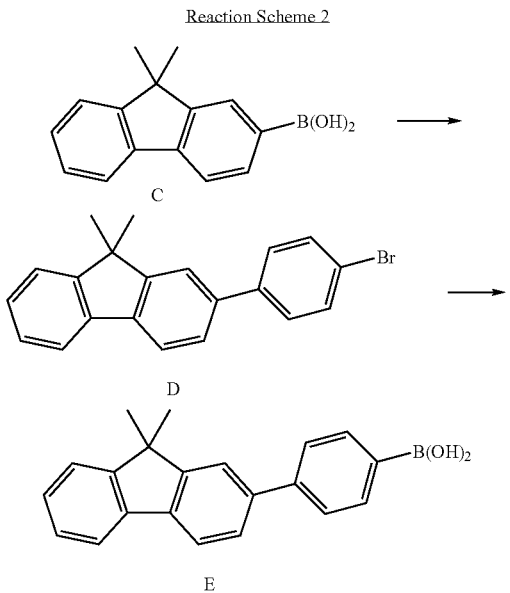

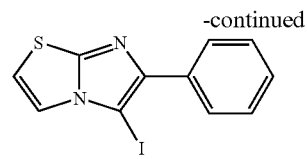

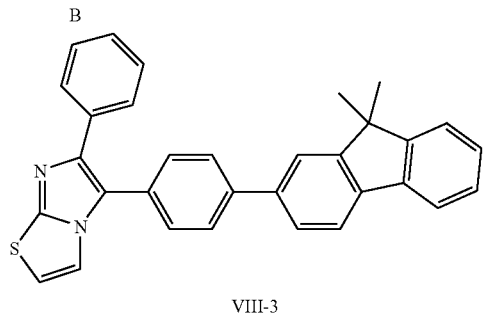

Synthesis of Intermediate (D)

100 mg (0.42 mmol) of intermediate (C) and 250 mg (1.05 mmol) of 1,4-dibromobenzene were dissolved in 5 ml of THF. 10 mg (0.008 mmol) of tetrakistriphenylphosphine-palladium and a solution of 580 mg (4.2 mmol) of K$_2$CO$_3$ in 3 ml of distilled water were sequentially added and stirred at 75° C. for 12 hours. The reaction solution was extracted three times using 10 ml of ethyl acetate each time. The collected organic phase was dried using magnesium sulfate and the solvent evaporated from the dried product. Then, the resulting product was purified by silica gel column chromatography to obtain 100 mg of intermediate (D) with a yield of 67%. The structure of intermediate (D) was identified by $^1$H NMR as follows: $^1$H NMR (CDCl$_3$, 400 MHz) δ (ppm) 7.78 (s, 1H), 7.75-7.73 (m, 1H), 7.60-7.55 (m, 3H), 7.54-7.50 (m, 3H), 7.46-7.43 (m, 1H), 7.37-7.31 (m, 2H), 1.53 (s, 6H).

Synthesis of Intermediate (E)

560 mg (1.6 mmol) of intermediate (D) was dissolved in 10 ml of THF, and 0.85 ml (2.08 mmol) of a solution of 2.5M n-butyl lithium dissolved in n-hexane butyl was added dropwise at −78° C. and stirred for 2 hours. 0.45 ml (4 mmol) of trimethyl borate was added to the reaction solution and stirred for 3 hours at the same temperature and further for 12 hours at room temperature. After adjusting the pH to pH 1 using an aqueous solution of 12M hydrochloric acid, the solution was stirred for 2 hours at room temperature. After adjusting the pH to pH 14 using a 4M NaOH solution, extraction was performed three times using 50 ml of diethyl ether each time. The collected organic phase was dried using magnesium sulfate and the solvent evaporated from the dried product. Then, the resulting product was purified by silica gel column chromatography to obtain 390 mg of intermediate (E) in white solid form with a yield of 77%.

Synthesis of Compound (VIII-3)

90 mg (0.276 mmol) of compound (B) and 95 mg (0.276 mmol) of intermediate (E) were reacted in the same manner as in the synthesis of compound (VIII-2) to obtain 112 mg of compound (VIII-3) with a yield of 87%. This compound was sublimated and purified at 300° C. in a 1-torr nitrogen atmosphere using a sublimating and purifying apparatus to obtain a white solid compound. The structure of this compound was identified by $^1$H NMR as follows:

$^1$H NMR (CDCl$_3$, 400 MHz) δ (ppm) 7.81 (d, 1H), 7.77-7.74 (m, 3H), 7.71-7.67 (m, 3H), 6.64 (dd, 1H), 7.56-7.52 (m, 2H), 7.48-7.44 (m, 2H), 7.37-7.28 (m, 4H), 7.27-

7.24 (m, 1H), 6.83 (d, 1H), 1.56 (s, 6H); $^{13}$C NMR (CDCl$_3$, 100 MHz) δ (ppm) 154.4, 153.9, 149.1, 143.7, 141.3, 139.3, 138.9, 138.7, 134.5, 129.4, 129.2, 128.3, 127.8, 127.6, 127.4, 127.2, 127.1, 126.0, 122.6, 122.5, 121.2, 120.4, 120.2, 117.5, 112.5, 46.9, 27.3.

Figure 3:
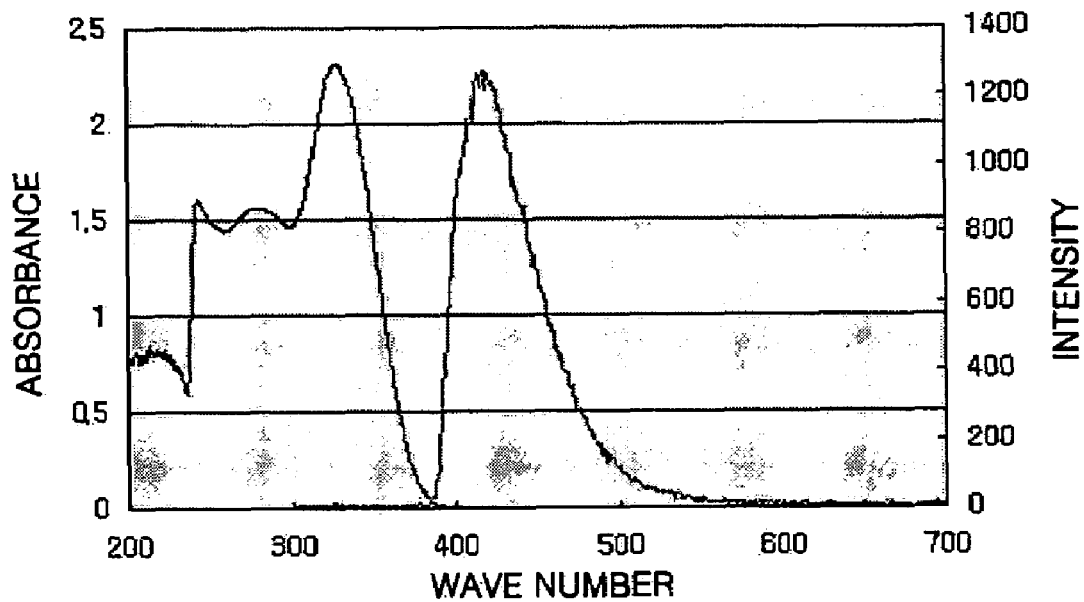
FIG. 3 is the PL spectrum of a solution containing compound (VIII-3) according to an embodiment of the present invention.

Compound (VIII-3) obtained in Specific Example 2 was diluted to 0.2 mM using CHCl$_3$ for UV spectrum measurement. The results showed that compound (VIII-3) has a maximum absorption peak at 326.5 nm. Compound (VIII-3) was diluted to 10 mM using CHCl$_3$ to measure its PL characteristics at 326.5 nm. The results showed that a maximum emission peak appears at 418 nm (FIG. 3). The color purity of the compound at this wavelength is CIE(x,y): 0.1664, 0.0562 in an NTSC chromaticity coordinate system.

Figure 4:
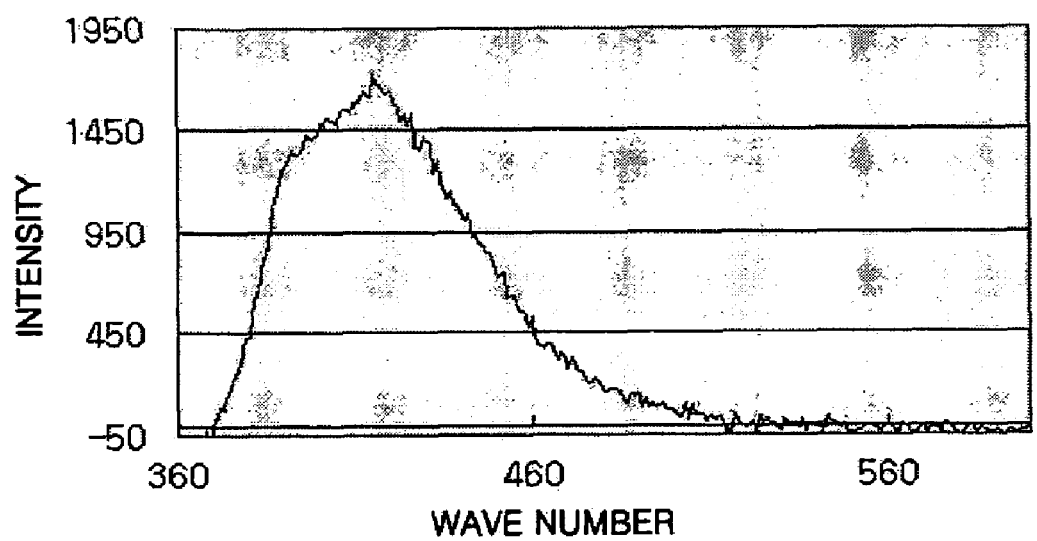
FIG. 4 is the PL spectrum of a thin film formed using compound (VIII-3) according to an embodiment of the present invention.
Figure 5:
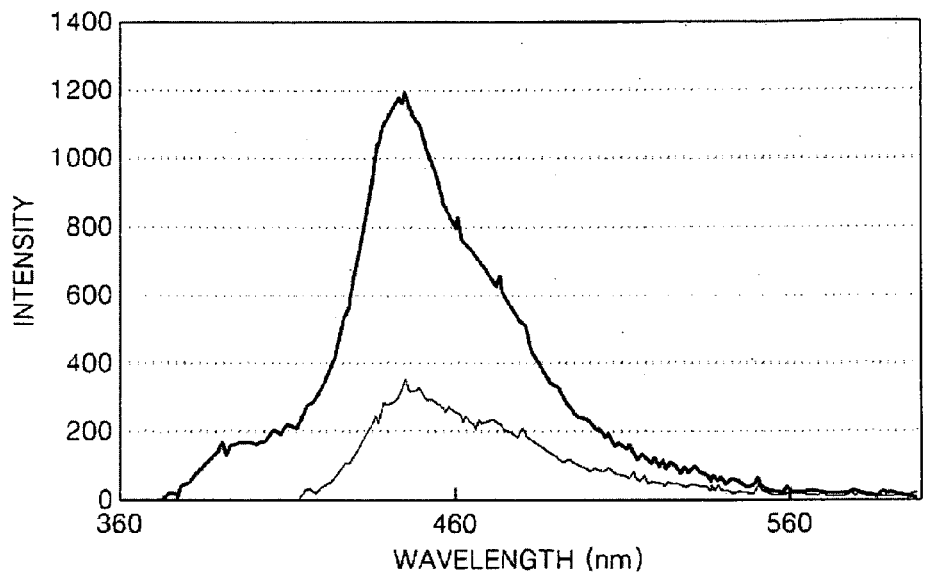
FIG. 5 is the PL spectrum of a thin film formed using compound (VIII-3) according to an embodiment of the present invention and polymethylmethacrylate.

A solution obtained by dissolving compound (VIII-3) and polymethylmethacrylate (PMMA) in a ratio of 15:1 by weight was spin-coated on a glass substrate (1.0T, 50 mm×50 mm) to form a thin film. The PL characteristics of the film were measured. As a result, a maximum emission peak appears at 425 nm (FIG. 4). The color purity of the film at this wavelength is CIE(x,y): 0.1594, 0.0264 in an NTSC chromaticity coordinate system. A thin film was coated using a mixture of compound (VIII-3) as a fluorescent host and 5% by weight of IDE 105 (Idemitsu Co., Southfield, Mich.) as a blue fluorescent dopant, and the PL characteristics of the thin film were measured and compared with the PL characteristics of blue fluorescent host IDE 140 (Idemitsu Co.) (FIG. 5). Compound (VIII-3) has a much greater maximum absorption peak at 444 nm than IDE-140.

AC-2 analysis of the compound, which is a UV absorption spectrum and ionization potential measuring system, showed that the HOMO (Highest Occupied Molecular Orbital) energy level was 5.79 eV, and the LOMO (Lowest Occupied Molecular Orbital) energy level was 2.64 eV.

Thermo gravimetric analysis (TGA) and differential scanning calorimetry (DSC) were performed using compound (VIII-3). The thermal analysis was performed in a N$_2$ gas atmosphere, the TGA was performed in a temperature range from room temperature to 600° C. at a rate of 10° C./min, and the DSC was performed in a temperature range from room temperature to 400° C.

Figure 6:
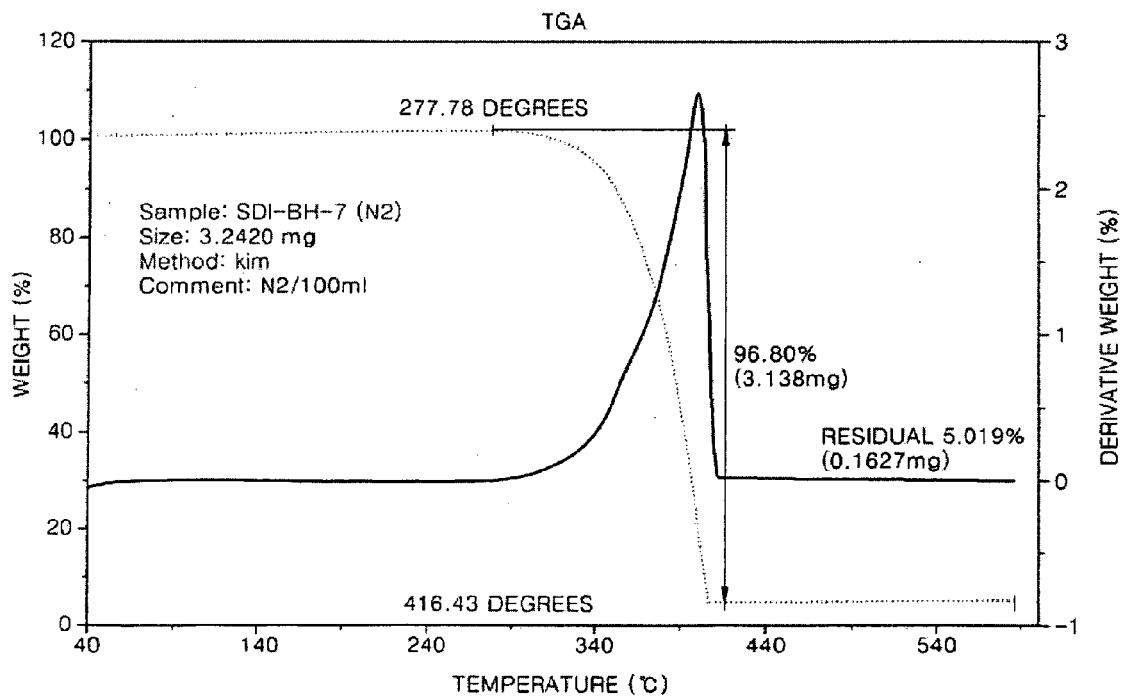
FIG. 6 is a graph illustrating the result of a thermo gravimetric analysis (TGA) using compound (VIII-3) according to an embodiment of the present invention.
Figure 7:
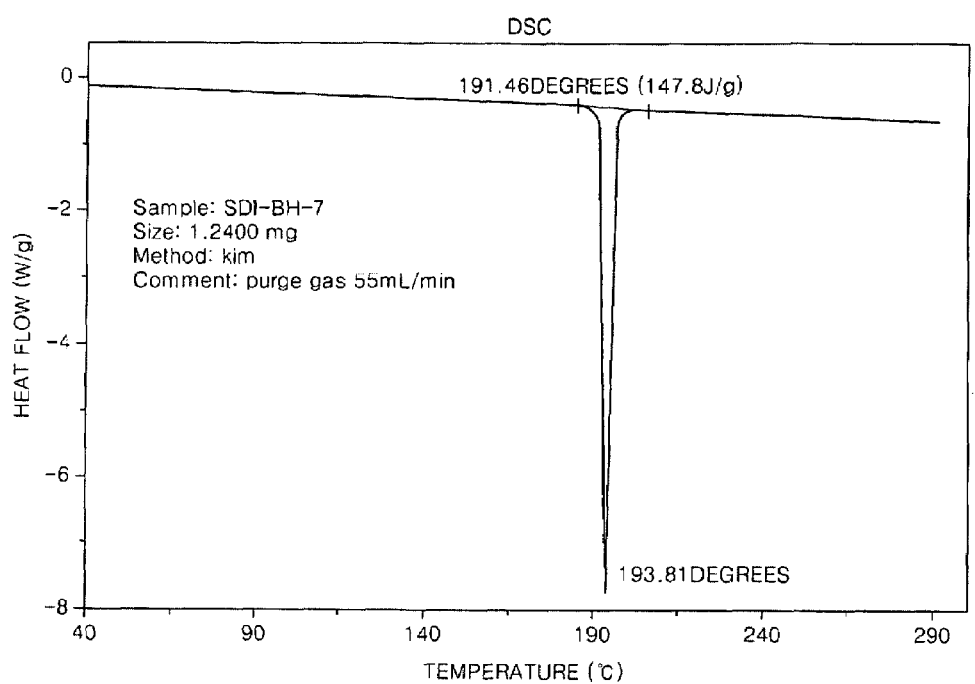
FIG. 7 is the differential scanning calorimetry (DSC) curve of compound (VIII-3) according to an embodiment of the present invention.

The analysis showed that compound (VIII-3) has a Td of 278° C., a Tg of 107° C., and a Tm of 194° C. (FIGS. 6 and 7).

Specific Example 3

Synthesis of Compound (VIII-5)

Compound (VIII-5) was synthesized according to Reaction scheme (3) below.

Reaction Scheme 3

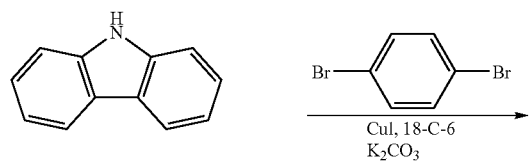

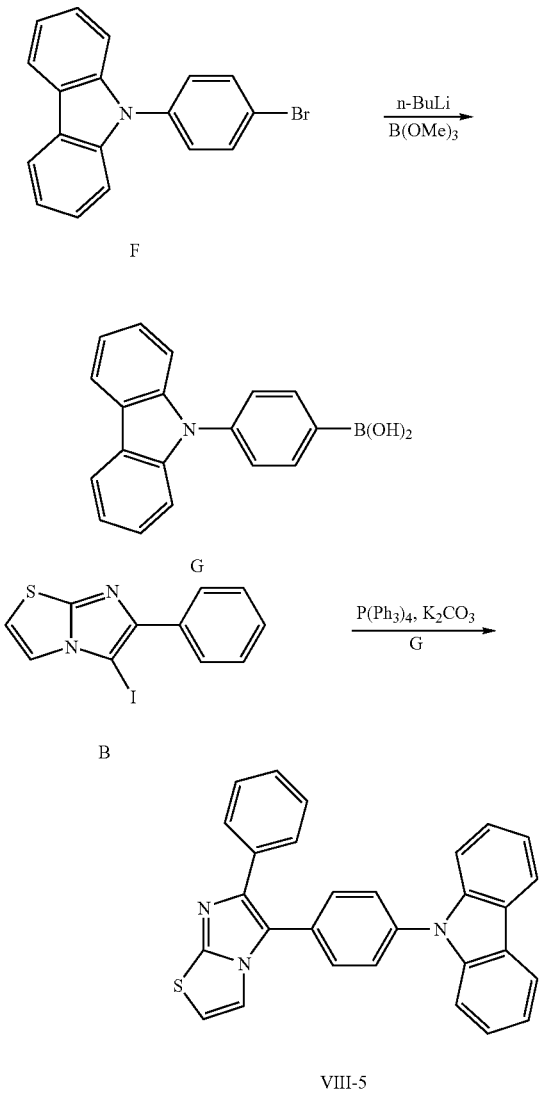

VIII-5

Synthesis of Intermediate (F)

335 mg (2 mmol) of carbazole, 1.2 g (5 mmol) of 1,4-dibromobenzene, 76 mg (0.4 mmol) of CuI, 1.1 g (8 mmol) of K$_2$CO$_3$ (1.1 g, 8 mmol), and 10 mg (0.04 mmol) of 18-Crown-6 were dissolved in 5 ml of DMPU (1,3-Dimethyl-3,4,5,6-tetrahydro-(1H)-pyrimidinone) and heated at 170° C. for 8 hours. After cooling to room temperature, the solid reaction product was filtered off, and a small amount of ammonia water was added to the filtrate, followed by washing three times using 10 ml of diethyl ether each time. The washed diethyl ether phase was dried using MgSO$_4$ under reduced pressure to obtain a crude product. The crude product was purified by silica gel column chromatography to obtain 480 mg of intermediate (F) in solid form with a yield of 75%. The compound was characterized using proton NMR as follows: $^1$H NMR (CDCl$_3$, 400 MHz) δ (ppm) 8.12 (d, 2H), 7.70 (d, 2H), 7.43-7.34 (m, 6H), 7.30-7.26 (m, 2H).

Synthesis of Intermediate (G)

200 mg (0.62 mmol) of intermediate (F) was dissolved in 3 ml of THF, and 0.325 ml (0.806 mmol) of a solution of 2.5M n-butyl lithium dissolved in n-hexane butyl was added dropwise at −78° C. and stirred for 2 hours. 0.2 ml (1.86 mmol) of trimethyl borate was added to the reaction solution and stirred for 3 hours at the same temperature and further for 12 hours at room temperature. After adjusting the pH to pH 1 using an aqueous solution of 12M hydrochloric acid, the solution was stirred for 2 hours at room temperature. After adjusting the pH to pH 14 using a 4M NaOH solution, extraction was performed three times using 50 ml of diethyl ether each time. The collected organic phase was dried using magnesium sulfate and the solvent evaporated from the dried product. Then, the resulting product was purified by silica gel column chromatography to obtain 145 mg of intermediate (G) in white solid form with a yield of 81%.

Synthesis of Compound (VIII-5)

28 mg (0.087 mmol) of intermediate (B) and 25 mg (0.087 mmol) of intermediate (G) were reacted in the same manner as in the synthesis of compound (VIII-2) to obtain 27 mg of compound (VIII-5) with a yield of 71%. The structure of this compound was identified by $^1$H NMR as follows: $^1$H NMR (CDCl$_3$, 400 MHz) a (ppm) 8.16 (d, 2H), 7.72-7.68 (m, 6H), 7.55-7.50 (m, 3H), 7.47-7.43 (m, 2H), 7.38-7.28 (m, 5H), 6.88 (d, 1H).

Compound (VIII-5) obtained in Specific Example 3 was diluted to 0.2 mM using CHCl$_3$ for UV spectrum measurement. The results showed that compound (VIII-5) has a maximum absorption peak at 323.5 nm.

Figure 8:
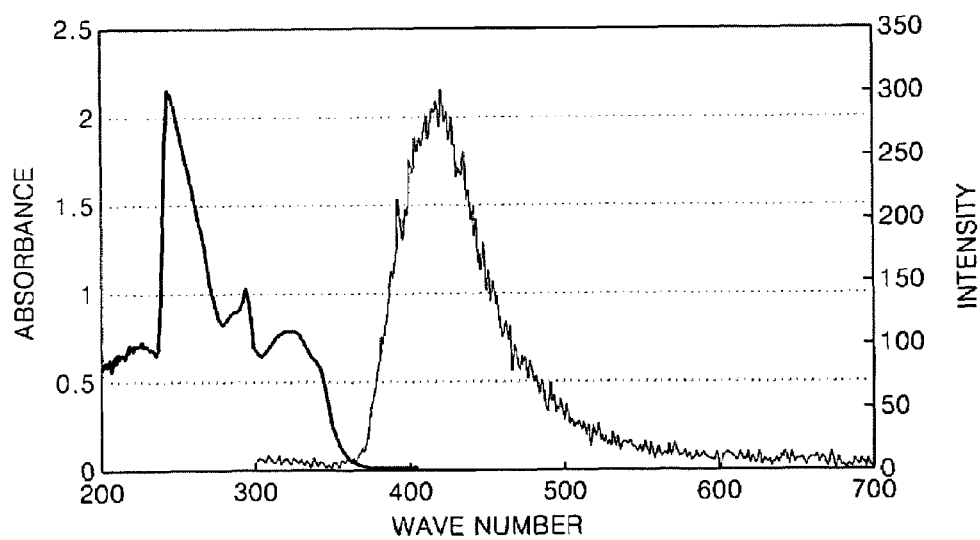
FIG. 8 is the PL spectrum of a solution containing compound (VIII-5) according to an embodiment of the present invention.

Compound (VIII-5) was diluted to 10 mM using CHCl$_3$ to measure its PL characteristics at 323.5 nm. The results showed that compound (VIII-5) has a maximum emission peak at 417 nm (FIG. 8). The color purity of the compound at this wavelength was CIE(x,y): 0.1981, 0.1183 in an NTSC chromaticity coordinate system.

Specific Example 4

Synthesis of Compound (VIII-8)

Compound (VIII-8) was synthesized according to Reaction scheme (4) below.

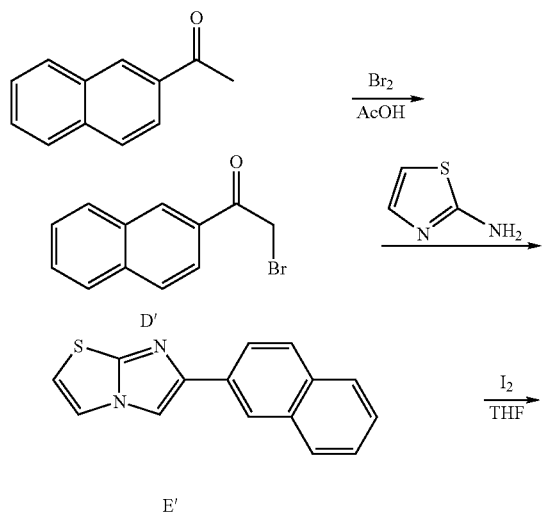

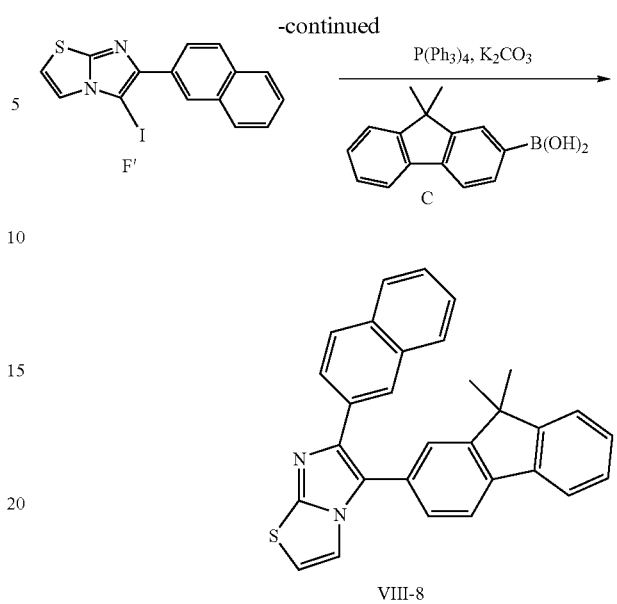

VIII-8

Synthesis of Intermediate (D')

17 g (100 mmol) of acetylnaphthalene was dissolved in 300 ml of CCl$_4$ and cooled to room temperature, and a catalytic amount of anhydrous HCl was added. 100 mmol of Br$_2$ was added dropwise and stirred at the same temperature for 3 hours and further at room temperature until the color from the bromide addition disappeared, followed by washing three times using ice water. The washed CCl$_4$ phase was dried using MgSO$_4$ and then under reduced pressure to obtain a crude product. The crude product was recrystallized using hexane to obtain 19.9 g of intermediate (D') in solid form with a yield of 80%.

Synthesis of Intermediate (E')

249 mg (1 mmol) of intermediate (D') was dissolved in 5 ml of DML and 0.1 g (1 mmol) of 2-aminothiazole in solid state was added to the solution, stirred for 5 hours at room temperature, and refluxed for 12 hours. The reaction product was distilled in a reduced pressure to remove the solvent, and 250 ml of dichloromethane was added to dissolve the remaining product. The pH of the solution was adjusted to pH 10 using a 10% sodium carbonate solution to separate the dichloromethane phase. The remaining aqueous phase was extracted twice using 10 ml of dichloromethane. The collected organic phase was dried using magnesium sulfate and the solvent evaporated from the dried product. Then, the resulting product was purified by silica gel column chromatography to obtain 218 mg of intermediate (E') with a yield of 87%. The compound was characterized using proton NMR as follows: $^1$H NMR (CDCl$_3$, 400 MHz) δ (ppm) 8.37 (s, 1H), 7.89-7.80 (m, 5H), 7.48-7.40 (m, 3H), 6.81 (d, 1H).

Synthesis of Intermediate (F')

200 mg (0.8 mmol) of intermediate (E') was dissolved in 4 ml of pyridine, and 300 mg (1.2 mmol) of iodine was added thereto and stirred for 5 hours at 50° C. A saturated oxalic acid solution was added to stop the reaction, and extraction was performed three times using 5 ml of dichloromethane. The collected organic phase was dried using magnesium sulfate and the solvent evaporated from the dried product. Then, the resulting product was purified by silica gel column chromatography to obtain 150 mg of intermediate (F') with a yield of 50%.

The compound was characterized using proton NMR as follows: $^1$H NMR (CDCl$_3$, 400 MHz) δ (ppm) 8.48 (s, 1H), 8.14 (dd, 1H), 7.93-7.81 (m, 3H), 7.49-7.45 (m, 3H), 6.93 (d, 1H).

Synthesis of Compound (VIII-8)

20 mg (0.053 mmol) of intermediate (F) and 14 mg (0.053 mmol) of intermediate (C) were reacted in the same manner as in the synthesis of compound (VIII-2) to obtain 18 mg of compound (VIII-8) with a yield of 75%. The structure of this compound was identified by $^1$H NMR as follows: $^1$H NMR (CDCl$_3$, 400 MHz) δ (ppm) 8.25 (s, 1H), 7.83 (d, 1H), 7.78-7.67 (m, 5H), 7.54-7.37 (m, 8H), 6.86 (d, 1H), 1.43 (s, 6H).

Compound (VIII-8) obtained in Specific Example 4 was diluted to 0.2 mM using CHCl$_3$ for UV spectrum measurement. The results showed that compound (VIII-8) has a maximum absorption peak at 328.5 nm.

Figure 9:
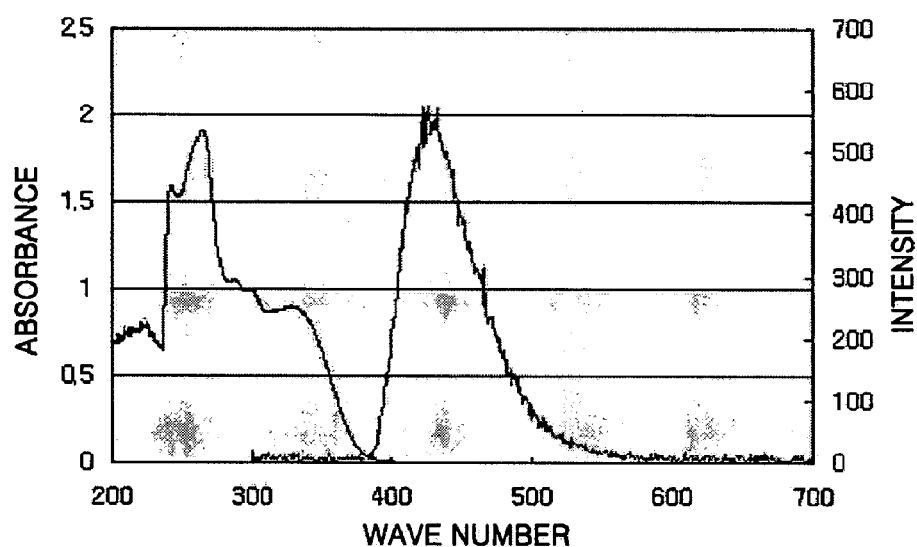
FIG. 9 is the UV spectrum and PL spectrum of a solution containing compound (VIII-5) according to an embodiment of the present invention.

Compound (VIII-8) was diluted to 10 mM using CHCl$_3$ to measure its PL characteristics at 328.5 nm. The results showed that compound (VIII-8) has a maximum emission peak at 426 nm (FIG. 9). The color purity of the compound at this wavelength is CIE(x,y): 0.1711, 0.0773 in an NTSC chromaticity coordinate system.

Specific Example 5

Synthesis of Compound (VIII-9)

20 mg (0.053 mmol) of intermediate (F') and 17 mg (0.053 mmol) of intermediate (E') were reacted in the same manner as in the synthesis of compound (VIII-2) to obtain 20 mg of compound (VIII-9) with a yield of 78%. The structure of this compound was identified by $^1$H NMR as follow: $^1$H NMR (CDCl$_3$, 400 MHz) δ (ppm) 8.25 (s, 1H), 7.83 (d, 1H), 7.78-7.67 (m, 5H), 7.54-7.37 (m, 8H), 6.86 (d, 1H), 1.43 (s, 6H).

Compound (VIII-9) obtained in Specific Example 5 was diluted to 0.2 mM using CHCl$_3$ for UV spectrum measurement. The results showed that compound (VIII-9) has a maximum absorption peak at 327 nm.

Figure 10:
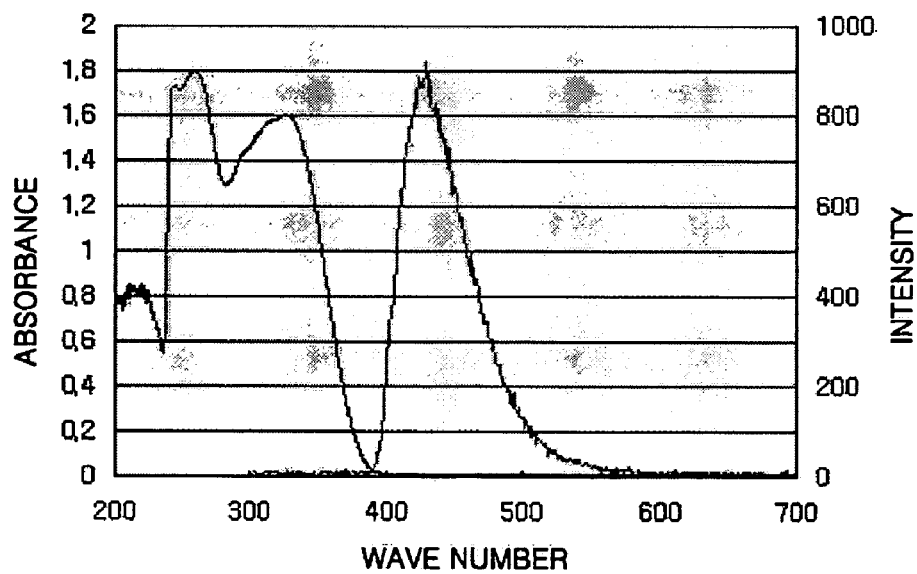
FIG. 10 is the UV spectrum and PL spectrum of a solution containing compound (VIII-9) according to an embodiment of the present invention.

Compound (VIII-9) was diluted to 10 mM using CHCl$_3$ to measure its PL characteristics at 327 nm. The results indicated that compound (VIII-9) has a maximum emission peak at 429 nm (FIG. 10). The color purity of the compound at this wavelength is CIE(x,y): 0.1661, 0.0718 in an NTSC chromaticity coordinate system.

Specific Example 6

Synthesis of Compound (VIII-11)

20 mg (0.053 mmol) of intermediate (F') and 14 mg (0.053 mmol) of intermediate (G) were reacted in the same manner as in the synthesis of compound (VIII-2) to obtain 18 mg of compound (VIII-11) with a yield of 75%. The structure of this compound was identified by $^1$H NMR as follows: $^1$H NMR (CDCl$_3$, 400 MHz) δ (ppm) 8.24 (s, 1H), 8.17 (d, 2H), 7.84-7.68 (m, 8H), 7.57 (d, 1H), 7.53 (d, 2H), 7.48-7.44 (m, 4H), 7.33 (dd, 2H), 6.92 (d, 1H).

Compound (VIII-11) obtained in Specific Example 6 was diluted to 0.2 mM using CHCl$_3$ for UV spectrum measurement. The results indicated that compound (VIII-11) has a maximum absorption peak at 325.5 nm.

Figure 11:
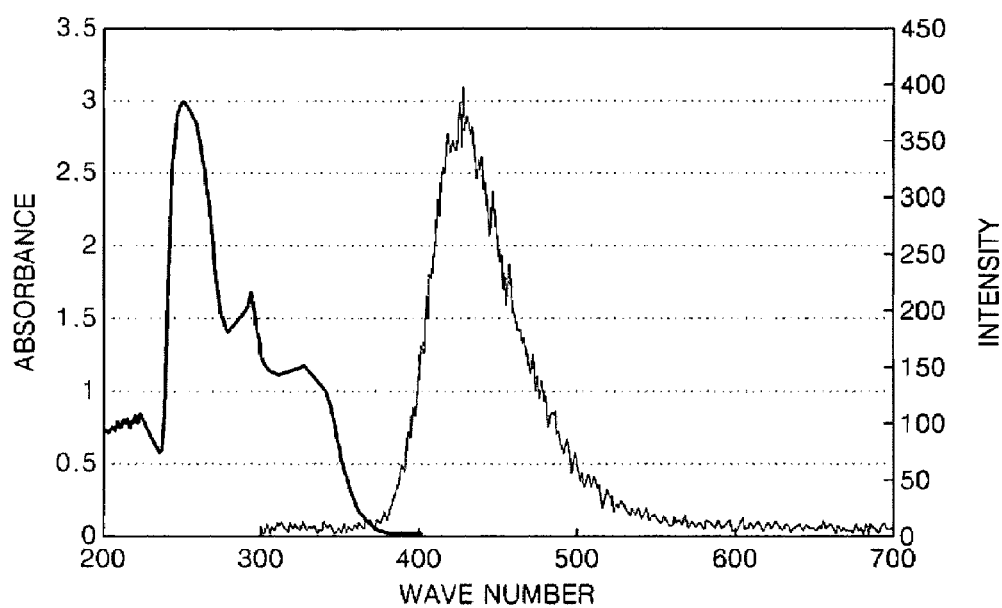
FIG. 11 is the UV spectrum and PL spectrum of a solution containing compound (VIII-11) according to an embodiment of the present invention.

Compound (VIII-11) was diluted to 10 mM using CHCl$_3$ to measure its PL characteristics at 325.5 nm. The results indicated that compound (VIII-11) has a maximum emission peak at 421 nm (FIG. 11). The color purity of the compound at this wavelength is CIE(x,y): 0.1823, 0.0941 in an NTSC chromaticity coordinate system.

As is apparent from the above-described results of the PL characteristics measurements performed on solutions and thin films, the imidazole ring-containing compounds have maximum absorption peaks in a range of about 417 nm to about 429 nm, and high color purities CIE(x,y) in a range of about 0.15 to about 0.19 for x coordinate and about 0.03 to about 0.11 for y coordinate in the NTSC chromaticity coordinate system.

Specific Example 7

An indium tin oxide (ITO) substrate (available from Corning Co., Corning, N.Y.) having a resistance of 10 Ω/cm$^2$ was used for an anode. A hole injecting layer was formed of IDE 406 (available from Idemitsu Co., Southfield, Mich.) on the anode to a thickness of 600 Å by vacuum deposition. Next, a hole transporting layer was formed of IDE 320 (available from Idemitsu Co.) on the hole injecting layer by vacuum deposition to a thickness of 300 Å by vacuum deposition. An electroluminescent layer was formed of a 90:10 mixture by weight of compound (VIII-2) and IDE 105 (available from Idemitsu Co.) on the hole transporting layer to a thickness of 300 Å by vacuum deposition.

Next, a hole blocking layer was formed of Balq on the electroluminescent layer to a thickness of 50 Å by vacuum deposition. An electron transporting layer was formed of Alq3 on the hole blocking layer to a thickness of 200 Å by vacuum deposition. LiF and Al were sequentially deposited on the electron transporting layer to a thickness of 10 Å and 3000 Å, respectively, by vacuum deposition to form a cathode, thereby resulting in a complete organic EL display device.

The luminance, efficiency, driving voltage, and color purity of the organic EL display device manufactured in Example 7 were measured. As a result, it was found that the organic EL display device has improved characteristics such as luminance, efficiency, driving voltage, and color purity.

As described above, an imidazole ring-containing compound of Formula (1) above according to the present invention may be used alone or in combination with a dopant as a material for organic films such as an electroluminescent layer. In addition, an organic EL display device with improved luminance, efficiency, driving voltage, and color purity may be manufactured using an organic film containing the imidazole ring-containing compound.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An imidazole ring-containing compound, comprising:

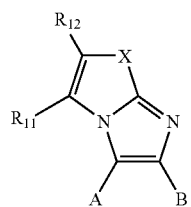

Formula 1 where A is selected from the group consisting of

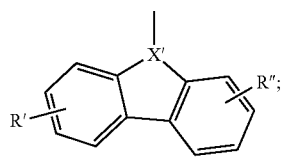

B is selected from the group consisting of

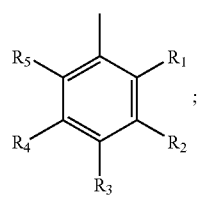

where X is; X' is selected from the group consisting of CR and N; where each of $R_1$ through $R_5$, $R_{11}$, and $R_{12}$ is independently selected from the group consisting of a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C2-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, where adjacent groups among $R_1$ through $R_5$, $R_{11}$, and $R_{12}$ can combine together to form a substituted or unsubstituted $C_2$-$C_{30}$ saturated or unsaturated ring; where each of R' and R", which are monosubstituted or multi-substituted groups, is selected from the group consisting of a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, and where R' and R" can combine together to form a saturated or unsaturated ring.

2. The imidazole ring-containing compound of claim 1, further represented by:

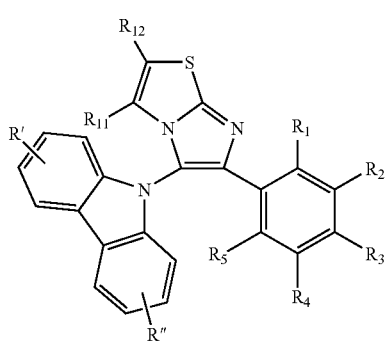

Formula 9 where each of $R_1$ through $R_5$ are independently selected from the group consisting of a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, where adjacent groups among $R_1$ through $R_5$, $R_{11}$, and $R_{12}$ can combine together to form a substituted or unsubstituted C2-C30 saturated or unsaturated ring, both $R_{11}$ and $R_{12}$ are hydrogen or combine together to form a substituted or unsubstituted C2-C30 saturated or unsaturated ring, and both R' and R" are hydrogen.

3. An organic electroluminesence display device comprising an organic film between a pair of electrodes, wherein the organic film is composed of an imidazole ring-containing compound, comprising:

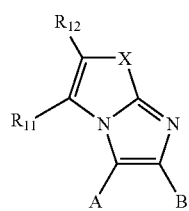

Formula 1 where A is selected from the group consisting of

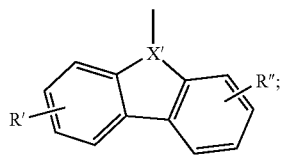

B is selected from the group consisting of

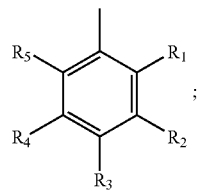

where X is S; X' is selected from the group consisting of CR and N; each of $R_1$ through $R_{11}$, and $R_{12}$ is independently selected from the group consisting of a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, wherein adjacent groups among $R_1$ through $R_5$, $R_{11}$, and $R_{12}$ can combine together to form a substituted or unsubstituted $C_2$-$C_{30}$ saturated or unsaturated ring;

where each of R' and R", which are monosubstituted or multi-substituted groups, is selected from the group consisting of hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, wherein R' and R" can combine together to form a saturated or unsaturated ring.

4. The organic electroluminescence display device of claim 3, wherein the organic film is an electroluminescent layer.

5. The organic electroluminescence display device of claim 4, wherein the electroluminescent layer further comprises a phosphorescent or fluorescent dopant emitting visible range light.

6. The organic electroluminescence display device of claim 3, wherein the organic film is a hole injecting layer or a hole transporting layer.

7. The organic electroluminescence display device of claim 3, wherein the compound of Formula (1) is further represented by:

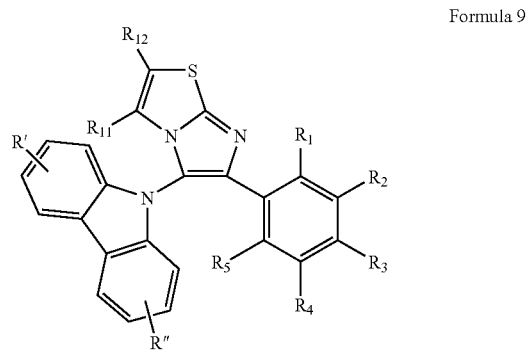

Formula 9 where each of $R_1$ through $R_5$, $R_{11}$, and $R_{12}$ is independently selected from the group consisting of a hydrogen, a substituted or unsubstituted C1-C30 alkyl group, a substituted or unsubstituted C1-C30 alkoxy group; a substituted or unsubstituted C4-C30 cycloalkyl group, a substituted or unsubstituted C6-C30 aryl group, a substituted or unsubstituted C6-C30 aryloxy group, a substituted or unsubstituted C2-C30 heteroacryl group, a substituted or unsubstituted C2-C30 heteroaryloxy group, a substituted or unsubstituted C6-C30 condensed polycyclic group, an amino group, a substituted or unsubstituted C1-C30 alkylamino group, a substituted or unsubstituted C6-C30 arylamino group, a cyano group, a nitro group, a hydroxy group, a halogen atom, a substituted or unsubstituted C6-C30 arylsulfonyl group, and a substituted or unsubstituted C1-C30 alkylsulfonyl group, wherein adjacent groups among $R_1$ through $R_5$, $R_{11}$, and $R_{12}$ can combine together to form a substituted or unsubstituted C2-C30 saturated or unsaturated ring, both $R_{11}$ and $R_{12}$ are hydrogen or combine together to form a substituted or unsubstituted C2-C30 saturated or unsaturated ring, and both R' and R" are hydrogen.

* * * * *